United States Patent
Roche et al.

(10) Patent No.: US 9,839,374 B2
(45) Date of Patent: Dec. 12, 2017

(54) SYSTEM AND METHOD FOR VERTEBRAL LOAD AND LOCATION SENSING

(75) Inventors: Martin Roche, Fort Lauderdale, FL (US); Marc Boillot, Plantation, FL (US); Marc Stein, Chandler, AZ (US)

(73) Assignee: Orthosensor Inc., Dania Beach, FL (US)

( * ) Notice: Subject to any disclaimer, the term of this patent is extended or adjusted under 35 U.S.C. 154(b) by 880 days.

(21) Appl. No.: 13/243,362

(22) Filed: Sep. 23, 2011

(65) Prior Publication Data

US 2013/0079679 A1 Mar. 28, 2013

(51) Int. Cl.
| | |
|---|---|
| A61B 5/103 | (2006.01) |
| A61B 5/107 | (2006.01) |
| A61B 5/00 | (2006.01) |
| A61F 2/46 | (2006.01) |
| A61F 2/44 | (2006.01) |
| A61F 2/28 | (2006.01) |
| A61F 2/30 | (2006.01) |

(52) U.S. Cl.
CPC ............ *A61B 5/103* (2013.01); *A61B 5/1036* (2013.01); *A61B 5/1071* (2013.01); *A61B 5/4566* (2013.01); *A61B 5/686* (2013.01); *A61F 2/4611* (2013.01); *A61F 2/4455* (2013.01); *A61F 2002/2835* (2013.01); *A61F 2002/30011* (2013.01); *A61F 2002/3085* (2013.01); *A61F 2002/4475* (2013.01); *A61F 2310/00023* (2013.01)

(58) Field of Classification Search
CPC .......... A61B 19/5244; A61B 2019/464; A61B 2019/5255
USPC ........................................ 600/301, 424, 594
See application file for complete search history.

(56) References Cited

U.S. PATENT DOCUMENTS

| | | |
|---|---|---|
| 3,573,782 A | 4/1971 | Williams |
| 3,727,616 A | 4/1973 | Lenzkes |
| 4,066,082 A | 1/1978 | Arcan et al. |
| 4,092,597 A | 5/1978 | Place |

(Continued)

FOREIGN PATENT DOCUMENTS

| | | |
|---|---|---|
| CN | 1509156 | 6/2004 |
| CN | 101254103 | 9/2006 |

(Continued)

OTHER PUBLICATIONS

International Search Report for PCT/US2012/056689 dated Feb. 25, 2013, 4 pages.

(Continued)

*Primary Examiner* — Sean Dougherty

(57) ABSTRACT

A load balance and alignment system is provided to assess load forces on the vertebra in conjunction with overall spinal alignment. The system includes a spine instrument having an electronic assembly and a sensorized head. The sensorized head can be inserted between vertebra and report vertebral conditions such as force, pressure, orientation and edge loading. A GUI is therewith provided to show where the spine instrument is positioned relative to vertebral bodies as the instrument is placed in the inter-vertebral space. The system can report optimal prosthetic size and placement in view of the sensed load and location parameters including optional orientation, rotation and insertion angle along a determined insert trajectory.

14 Claims, 11 Drawing Sheets

(56) References Cited

U.S. PATENT DOCUMENTS

| | | |
|---|---|---|
| 4,127,110 A | 11/1978 | Bullara |
| 4,277,758 A | 7/1981 | Mishiro |
| 4,480,485 A | 11/1984 | Bradshaw et al. |
| 4,524,766 A | 6/1985 | Petersen |
| 4,731,762 A | 3/1988 | Hanks |
| 4,764,804 A | 8/1988 | Sahara et al. |
| 4,848,164 A | 7/1989 | Quarve et al. |
| 4,857,893 A | 8/1989 | Carroll |
| 4,864,463 A | 9/1989 | Shkedi et al. |
| 4,899,761 A | 2/1990 | Brown et al. |
| 4,902,958 A | 2/1990 | Cook, II |
| 4,920,279 A | 4/1990 | Charlet et al. |
| 4,986,281 A | 1/1991 | Preves et al. |
| 5,042,489 A | 8/1991 | Weiner et al. |
| 5,119,676 A | 6/1992 | Bower et al. |
| 5,285,677 A * | 2/1994 | Oehler ................ 73/24.01 |
| 5,456,724 A | 10/1995 | Yen et al. |
| 5,470,354 A | 11/1995 | Hershberger et al. |
| 5,650,571 A | 7/1997 | Freud et al. |
| 5,733,292 A | 3/1998 | Gustilo et al. |
| 5,900,592 A | 5/1999 | Sohns et al. |
| 6,033,370 A | 3/2000 | Reinbold et al. |
| 6,070,469 A | 6/2000 | Taniguchi et al. |
| 6,072,784 A | 6/2000 | Agrawal et al. |
| 6,159,611 A | 12/2000 | Lee et al. |
| 6,165,142 A | 12/2000 | Bar |
| 6,425,920 B1 | 7/2002 | Hamada |
| 6,429,585 B1 | 8/2002 | Kitazume et al. |
| 6,443,891 B1 | 9/2002 | Grevious |
| 6,447,448 B1 | 9/2002 | Ishikawa et al. |
| 6,621,278 B2 | 9/2003 | Ariav |
| 6,739,068 B1 | 5/2004 | Rinner |
| 6,796,988 B2 | 9/2004 | Melkent et al. |
| 6,856,141 B2 | 2/2005 | Ariav |
| 6,859,661 B2 * | 2/2005 | Tuke ................... 600/424 |
| 6,993,393 B2 | 1/2006 | Von Arx et al. |
| 7,035,077 B2 | 4/2006 | Brendel |
| 7,080,554 B2 | 7/2006 | Ariav et al. |
| 7,097,662 B2 | 8/2006 | Evans, III et al. |
| 7,153,281 B2 | 12/2006 | Holmes |
| 7,173,749 B2 | 2/2007 | Maleki et al. |
| 7,195,645 B2 | 3/2007 | Disilvestro et al. |
| 7,215,599 B2 | 5/2007 | Nishimori et al. |
| 7,283,867 B2 | 10/2007 | Strother et al. |
| 7,347,817 B2 | 3/2008 | Glukhovsky et al. |
| 7,378,916 B2 | 5/2008 | Oita et al. |
| 7,384,403 B2 | 6/2008 | Sherman |
| 7,396,336 B2 | 7/2008 | Orszulak et al. |
| 7,412,897 B2 | 8/2008 | Crottet et al. |
| 7,442,196 B2 | 10/2008 | Fisher et al. |
| 7,454,972 B2 | 11/2008 | Heyman et al. |
| 7,477,926 B2 | 1/2009 | McCombs |
| 7,519,422 B2 | 4/2009 | Lippert et al. |
| 7,559,951 B2 | 7/2009 | DiSilvestro et al. |
| 7,575,602 B2 | 8/2009 | Amirouche et al. |
| 7,578,821 B2 | 8/2009 | Fisher et al. |
| 7,615,055 B2 | 11/2009 | DiSilvestro |
| 7,630,774 B2 | 12/2009 | Karni et al. |
| 7,632,283 B2 | 12/2009 | Heldreth |
| 7,668,201 B2 | 2/2010 | Sharony et al. |
| 7,725,288 B2 | 5/2010 | Boillot |
| 7,769,947 B2 | 8/2010 | Ranganathan et al. |
| 7,819,826 B2 | 10/2010 | Diederich et al. |
| 7,918,887 B2 | 4/2011 | Roche |
| 8,000,926 B2 | 8/2011 | Roche |
| 8,098,544 B2 | 1/2012 | Roche |
| 8,099,168 B2 | 1/2012 | Roche |
| 8,141,437 B2 | 3/2012 | Amirouche et al. |
| 8,167,823 B2 | 5/2012 | Nycz |
| 8,169,185 B2 | 5/2012 | Partovi et al. |
| 8,197,549 B2 | 6/2012 | Amirouche et al. |
| 8,211,041 B2 | 7/2012 | Fisher et al. |
| 8,270,253 B1 | 9/2012 | Roche |
| 8,295,920 B2 | 10/2012 | Bouton et al. |
| 8,372,147 B2 | 2/2013 | Roche |
| 8,372,153 B2 | 2/2013 | Roche |
| 8,421,642 B1 | 4/2013 | McIntosh et al. |
| 8,444,654 B2 | 5/2013 | Roche |
| 8,449,556 B2 | 5/2013 | Roche |
| 8,494,805 B2 | 7/2013 | Roche |
| 8,498,711 B2 | 7/2013 | Roche |
| 2002/0049394 A1 | 4/2002 | Roy et al. |
| 2003/0004518 A1 | 1/2003 | Perren et al. |
| 2003/0036713 A1 | 2/2003 | Bouton et al. |
| 2003/0036764 A1 | 2/2003 | Hamada |
| 2003/0069644 A1 | 4/2003 | Kovacevic et al. |
| 2003/0114898 A1 | 6/2003 | Von Arx et al. |
| 2003/0187351 A1 | 10/2003 | Franck et al. |
| 2004/0011365 A1 | 1/2004 | Govari et al. |
| 2004/0064073 A1 | 4/2004 | Heldreth |
| 2004/0131013 A1 | 7/2004 | Ise et al. |
| 2004/0152970 A1 | 8/2004 | Hunter et al. |
| 2004/0184351 A1 | 9/2004 | Nishimori et al. |
| 2004/0199168 A1 | 10/2004 | Bertagnoli et al. |
| 2004/0215079 A1 | 10/2004 | Omura et al. |
| 2005/0010299 A1 | 1/2005 | Disilvestro |
| 2005/0010302 A1 | 1/2005 | Dietz et al. |
| 2005/0119709 A1 | 6/2005 | Gauglitz et al. |
| 2005/0234555 A1 | 10/2005 | Sutton |
| 2005/0252294 A1 | 11/2005 | Ariav |
| 2005/0267485 A1 | 12/2005 | Cordes et al. |
| 2005/0273170 A1 | 12/2005 | Navarro et al. |
| 2006/0069436 A1 | 3/2006 | Sutton et al. |
| 2006/0132120 A1 | 6/2006 | Luber et al. |
| 2006/0161051 A1 | 7/2006 | Terrill-Grisoni et al. |
| 2006/0195109 A1 | 8/2006 | McGahan et al. |
| 2006/0206014 A1 | 9/2006 | Ariav |
| 2006/0235424 A1 * | 10/2006 | Vitale et al. ................ 606/90 |
| 2006/0241569 A1 | 10/2006 | DiSilvestro |
| 2007/0129776 A1 | 6/2007 | Robins et al. |
| 2007/0168051 A1 * | 7/2007 | Bronnenberg ..... H04N 21/4332 700/20 |
| 2007/0168851 A1 * | 7/2007 | Hunt ............... H05B 37/029 715/209 |
| 2007/0168852 A1 * | 7/2007 | Erol ................ G06F 17/30044 715/234 |
| 2007/0168862 A1 * | 7/2007 | Hunt ............... H05B 37/029 715/705 |
| 2007/0174758 A1 * | 7/2007 | Ando ............. G11B 20/00086 715/203 |
| 2007/0174917 A1 * | 7/2007 | Guruswamy ....... H04L 63/1433 726/25 |
| 2007/0233065 A1 | 10/2007 | Donofrio et al. |
| 2007/0233267 A1 | 10/2007 | Amirouche et al. |
| 2007/0234819 A1 | 10/2007 | Amirouche et al. |
| 2007/0242652 A1 | 10/2007 | Dahlman et al. |
| 2007/0244488 A1 * | 10/2007 | Metzger et al. ................ 606/90 |
| 2007/0258674 A1 | 11/2007 | Wang |
| 2008/0082118 A1 | 4/2008 | Edidin et al. |
| 2008/0129486 A1 | 6/2008 | Jeckelmann et al. |
| 2008/0132783 A1 * | 6/2008 | Revie et al. ................ 600/426 |
| 2008/0133016 A1 | 6/2008 | Heinz |
| 2008/0191584 A1 | 8/2008 | Malkin |
| 2008/0228195 A1 | 9/2008 | Von Jako et al. |
| 2008/0228231 A1 | 9/2008 | Raphael et al. |
| 2009/0005708 A1 | 1/2009 | Johanson |
| 2009/0015270 A1 | 1/2009 | Hayakawa et al. |
| 2009/0112207 A1 | 4/2009 | Walker et al. |
| 2009/0167719 A1 * | 7/2009 | Woolley ................ 345/174 |
| 2010/0010494 A1 | 1/2010 | Quirno |
| 2010/0022874 A1 | 1/2010 | Wang et al. |
| 2010/0076505 A1 | 3/2010 | Borja |
| 2010/0100130 A1 | 4/2010 | Carl et al. |
| 2010/0151946 A1 | 6/2010 | Wilson et al. |
| 2010/0198067 A1 | 8/2010 | Mahfouz et al. |
| 2010/0198275 A1 | 8/2010 | Chana et al. |
| 2010/0204575 A1 | 8/2010 | Roche |
| 2010/0204955 A1 | 8/2010 | Roche |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0320973 A1 | 12/2010 | Nishida |

(56) References Cited

U.S. PATENT DOCUMENTS

| | | |
|---|---|---|
| 2010/0331633 A1 | 12/2010 | Stein |
| 2010/0331680 A1 | 12/2010 | Stein et al. |
| 2010/0331683 A1 | 12/2010 | Stein et al. |
| 2010/0331737 A1 | 12/2010 | Stein et al. |
| 2010/0331738 A1 | 12/2010 | Stein et al. |
| 2011/0029913 A1 | 2/2011 | Boillot |
| 2011/0032184 A1 | 2/2011 | Roche |
| 2011/0060220 A1 | 3/2011 | Roche |
| 2011/0092972 A1 | 4/2011 | Allen |
| 2011/0102455 A1* | 5/2011 | Temple .................. 345/619 |
| 2011/0160572 A1 | 6/2011 | McIntosh |
| 2011/0160616 A1 | 6/2011 | Stein et al. |
| 2011/0160738 A1 | 6/2011 | McIntosh et al. |
| 2011/0213221 A1* | 9/2011 | Roche .................. 600/301 |
| 2011/0257491 A1 | 10/2011 | Robertson et al. |
| 2012/0016362 A1 | 1/2012 | Heinrich et al. |
| 2012/0035868 A1 | 2/2012 | Roche |
| 2012/0152017 A1 | 6/2012 | Stein et al. |
| 2012/0209117 A1 | 8/2012 | Roche |
| 2012/0277752 A1 | 11/2012 | Wasielewski |
| 2013/0225982 A1 | 8/2013 | Roche |

FOREIGN PATENT DOCUMENTS

| | | |
|---|---|---|
| CN | 1960680 | 5/2007 |
| CN | 101106958 | 1/2008 |
| CN | 101254103 | 9/2008 |
| CN | 101426453 | 5/2009 |
| CN | 101528122 | 9/2009 |
| CN | 101869504 | 10/2010 |
| CN | 101917918 | 12/2010 |
| EP | 1800097 | 5/2008 |
| EP | 1800097 B1 | 5/2008 |
| JP | 3267825 | 3/2002 |
| JP | 2007037361 | 2/2007 |
| WO | 03005877 | 1/2003 |
| WO | 2006098759 | 9/2006 |
| WO | 2006098759 A1 | 9/2006 |
| WO | 2008120215 | 10/2008 |
| WO | 2008120215 A2 | 10/2008 |

OTHER PUBLICATIONS

International Search Report for PCT/US2012/056743 dated Mar. 27, 2013, 4 pages.

International Search Report for PCT/US2012/056702 dated Feb. 27, 2013, 7 pages.

International Search Report for PCT/US2012/056758 dated Mar. 28, 2013, 5 pages.

International Search Report for PCT/US2012/056748 dated Mar. 27, 2013, 4 pages.

International Search Report for PCT/US2012/056740 dated Feb. 26, 2013, 4 pages.

International Search Report and Written Opinion for PCT/US2014055521 dated Dec. 19, 2014.

E. Lou et al., Wireless Surgical Tools for Mechanical Measurements during Scoliosis Surgery; Proceedings of the 2005 IEEE, Engineering in Medicine and Biology 27th Annual Conference, Shanghai, China Sep. 1-4, 2005, pp. 7131-7134 (Sep. 2005).

Miyazaki S et al. "Capacitive transducer for continuous measurement of vertical foot force" Medical and Biological Engineering and Computing, Springer, Heidelberg, DE vol. 22, No. 4, Jul. 1, 1994, pp. 309-216, XP002133117.

International Search Report and Written Opinion for PCT/US2014/055521 dated Dec. 19, 2014. Dec. 19, 2014.

International Search Report for PCT/US2012/056689 dated Feb. 25, 2013. Feb. 25, 2013.

International Search Report for PCT/US2012/056743 dated Mar. 27, 2013. Mar. 27, 2013.

International Search Report for PCT/US2012/056702 dated Feb. 27, 2013. Feb. 27, 2013.

International Search Report for PCT/US2012/056758 dated Mar. 28, 2013. Mar. 28, 2013.

International Search Report for PCT/US2012/056748 dated Mar. 27, 2013. Mar. 27, 2013.

International Search Report for PCT/US2012/056740 dated Feb. 26, 2013. Feb. 26, 2013.

E. Lou et al., Wireless Surgical Tools for Mechanical Measurements during Scoliosis Surgery; Proceedings of the 2005 IEEE, Engineering in Medicine and Biology 27th Annual Conference, Shanghai, China Sep. 1-4, 2005, pp. 7131-7134 (Sep. 2005). Sep. 1, 2005.

Miyazaki S et al: "Capacitive transducer for continuous measurement of vertical foot force", Medical and Biological Engineering and Computing, Springer, Heildelberg, DE, vol. 22, No. 4, Jul. 1, 1994, pp. 309-216, XP002133117 Jul. 1, 1984.

E. Lou et al., Wireless Surgical Tools for Mechanical Measurements during Scoliosis Surgery, Proceedings of the 2005 IEEE Engineering in Medicine and Biology 27th Annual Conference Shanghai, China Sep. 1-4, 2005.

* cited by examiner

SYSTEM AND METHOD FOR VERTEBRAL LOAD AND LOCATION SENSING

FIELD

The present invention pertains generally to surgical electronics, and particularly to methods and devices for assessing alignment and surgical implant parameters during spine surgery and long-term implantation.

BACKGROUND

The spine is made up of many individual bones called vertebrae, joined together by muscles and ligaments. Soft intervertebral discs separate and cushion each vertebra from the next. Because the vertebrae are separate, the spine is flexible and able to bend. Together the vertebrae, discs, muscles, and ligaments make up the vertebral column or spine. The spine varies in size and shape, with changes that can occur due to environmental factors, health, and aging. The healthy spine has front-to-back curves, but deformities from normal cervical lordosis, thoracic kyphosis, and lumbar lordosis conditions can cause pain, discomfort, and difficulty with movement. These conditions can be exacerbated by herniated discs, which can pinch nerves.

There are many different causes of abnormal spinal curves and various treatment options from therapy to surgery. The goal of the surgery is a usually a solid fusion of the curved part of the spine. A fusion is achieved by operating on the spine, adding bone graft, and allowing the vertebral bones and bone graft to slowly heal together to form a solid mass of bone. Alternatively, a spinal cage is commonly used that includes bone graft for spacing and fusing vertebrae together. The bone graft may come from a bone bank or the patient's own hipbone. The spine can be substantially straightened with metal rods and hooks, wires or screws via instrumented tools and techniques. The rods or sometimes a brace or cast hold the spine in place until the fusion has a chance to heal.

BRIEF DESCRIPTION OF THE DRAWINGS

Various features of the system are set forth with particularity in the appended claims. The embodiments herein, can be understood by reference to the following description, taken in conjunction with the accompanying drawings, in which:

DETAILED DESCRIPTION

Figure 1:
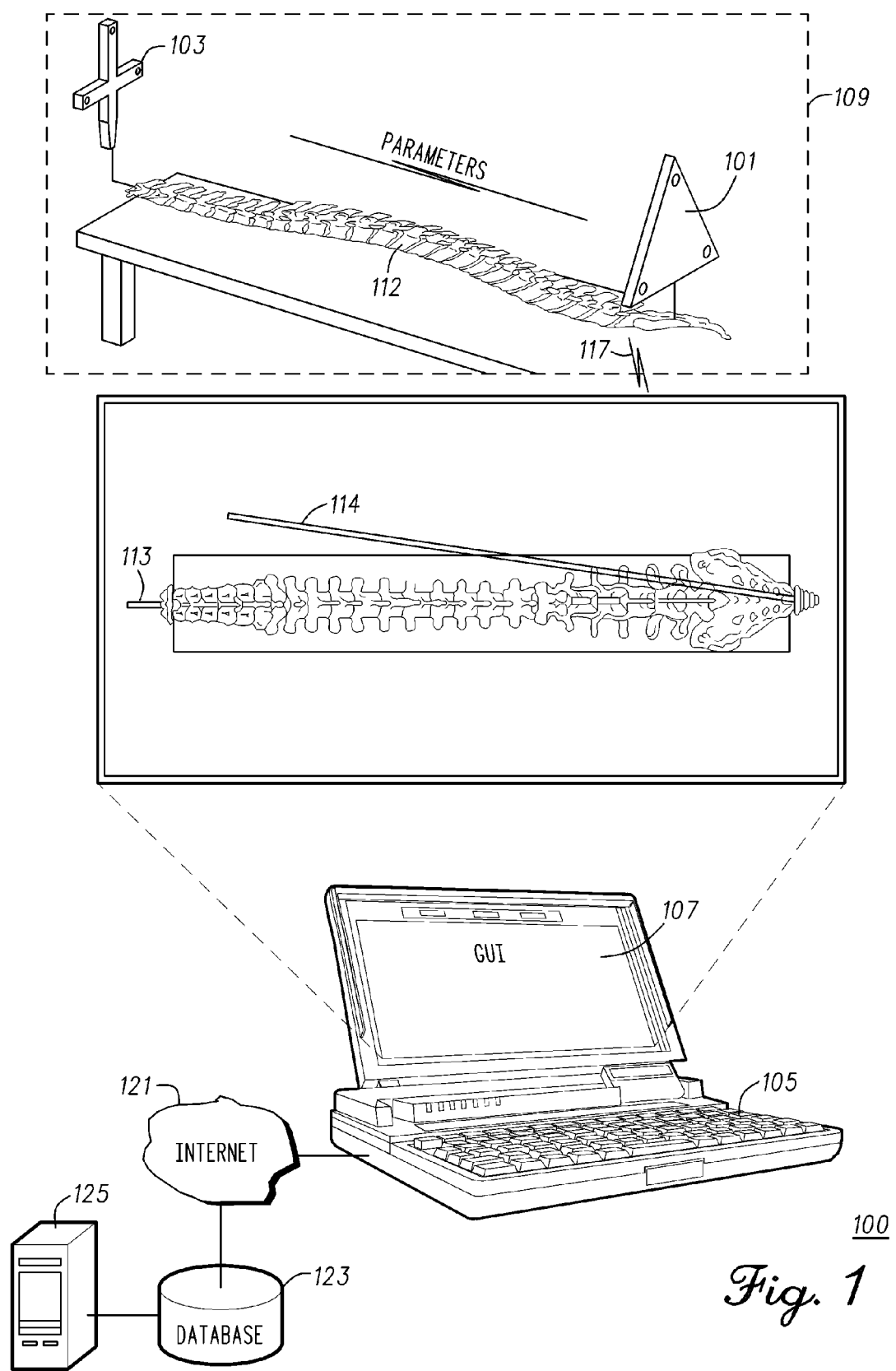
FIG. 1 illustrates a spinal alignment system in accordance with an example embodiment.

While the specification concludes with claims defining the features of the embodiments of the invention that are regarded as novel, it is believed that the method, system, and other embodiments will be better understood from a consideration of the following description in conjunction with the drawing figures, in which like reference numerals are carried forward.

As required, detailed embodiments of the present method and system are disclosed herein. However, it is to be understood that the disclosed embodiments are merely exemplary, which can be embodied in various forms. Therefore, specific structural and functional details disclosed herein are not to be interpreted as limiting, but merely as a basis for the claims and as a representative basis for teaching one skilled in the art to variously employ the embodiments of the present invention in virtually any appropriately detailed structure. Further, the terms and phrases used herein are not intended to be limiting but rather to provide an understandable description of the embodiment herein.

Broadly stated, embodiments of the invention are directed to a system and method for vertebral load and location sensing. A spine measurement system comprises a receiver and a plurality of wands coupled to a remote display that visually presents positional information. The wands can be placed on vertebra, or thereto touched, to report various aspects of spinal alignment. The positional information identifies an orientation and location of a wand and corresponding vertebrae of the spine. The system provides overall alignment plus the ability to track vertebral movement during a surgical operation. The system can propose and present intra-operative spine corrections in response to positional information captured during the procedure and previously recorded positional data related to a pre-operative spine condition.

The spine measurement system further includes a load balance and alignment system to assess load forces on the vertebra in conjunction with overall spinal alignment. The system includes a spine instrument having an electronic assembly and a sensorized head assembly that can articulate within a vertebral space. The sensorized head can be inserted between vertebra and report vertebral conditions such as force, pressure, orientation and edge loading. A GUI is used in conjunction therewith to show where the spine instrument is positioned relative to vertebral bodies as the instrument is placed in the inter-vertebral space during the surgical procedure. The system can report optimal prosthetic size and placement in view of the sensed load and location parameters including optional orientation, rotation and insertion angle along a determined insert trajectory.

An insert instrument is also provided herein with the load balance and alignment system for inserting a vertebral component such as a spine cage or pedicle screw. The system in view of previously captured parameter measurements can check and report if the instrument is edge loading during an insertion. It shows tracking of the insert instrument with the vertebral component and provides visual guidance and feedback based on positional and load sensing parameters. The system shows three-dimensional (3D) tracking of the insert instrument in relation to one or more vertebral bodies whose orientation and position are also modeled in 3D.

FIG. 1 illustrates a spinal alignment system 100 in a non-limiting example. The system 100 comprises a wand 103 and a receiver 101 that can be communicatively coupled to a remote system 105. In general, one or more wands communicate with the receiver 101 to determine positional information that includes one of an orientation, rotation, angle, and location of a spinal region. The receiver 101 transmits positional information or data 117 regarding the wand 103 to the remote system 105. The positional information includes orientation and translation data used to assess an alignment (or predetermined curvature) of the spine 112. The remote system 105 can be a laptop or mobile workstation that presents a Graphical User Interface (GUI) 107. The GUI 107 contains a workflow that shows the spine 112 and reports spinal alignment in view of positional information. As one example, the user interface can show an existing alignment 114 of the spinal vertebrae with respect to a post-surgical target alignment 113.

The alignment system 100 can be communicatively coupled to a database 123 system such as a server 125 to provide three-dimensional (3D) imaging (e.g., soft tissue) and 3D models (e.g., bone) captured prior to, or during, surgery. The 3D imaging and models can be used in conjunction with the positional information to establish relative location and orientation. The server 125 may be local in near vicinity or remotely accessed over the internet 121. As one example, the server 125 provides 3D spine and vertebra models. A CAT scanner (not shown) can be employed to produce a series of cross-sectional x-ray images of a selected part of the body. A computer operates the scanner, and the resulting picture represents a slice of the body. The server 125 produces a three-dimensional (3D) model from the slices. The server 125 can also provide 3D models generated from Magnetic Resonance Imaging (MRI) scanners (not shown). The server 125 may also support fluoroscopic imaging to provide real-time moving images of the internal structures of a patient with respect to the alignment system 100 devices through the use of X-ray source (not shown) and fluorescent screen.

The spine alignment system 100 reports overall alignment and instrument (e.g., wand 103 and receiver 101) orientation plus the ability to track isolated vertebral movement. The receiver 101 precisely tracks the location of the wand 103 at a particular vertebra and along the spine 112 to determine the positional information. The receiver 101 is shown coupled (e.g., pinned, screwed, affixed) to the sacrum. However, it can be located anywhere along the vertebrae of the spine. Alternatively, it can be mounted to a stand in the vicinity of the spine 112. The wand 103 and receiver 101 are sensorized devices that can transmit their position via ultrasonic, optical, or electromagnetic sensing. In the example, the wand 103 and the receiver 102 utilize ultrasonic transducers and are line of sight devices. The sensors may be externally mounted on the wand 103 away from the wand tip, or in some cases, within the wand tip. The wand 103 can be held in the hand or affixed to the spine via a mechanical assembly. In one embodiment, the components for generating all alignment measurements (e.g. receiver 101 and wand 103) reside within a sterile field 109 of an operating room. The sterile field 109 can also be called a surgical field. Typically, the remote system 105 is outside the sterile field 109 of the operating room. The components used within the sterile filed 109 can be designed for a single use. In the example, the wand 103, receiver 102, or both are disposed of after being used intra-operatively.

One example of an ultrasonic sensing device is disclosed in U.S. patent application Ser. No. 11/683,410 entitled "Method and Device for Three-Dimensional Sensing" filed Mar. 7, 2007 the entire contents of which are hereby incorporated by reference. One example of optical sensing includes three or four active IR reflectors on the wand 103 with corresponding high-speed camera elements on the receiver 101 for optical tracking, or alternatively high-speed photo-diode elements for detecting incident light beam angles and thereafter triangulating a wand position. One example of electromagnetic sensing includes metallic spheres on the wand whose spatial location is determined by evaluating changes in generated magnetic field strengths on the receiver 103.

Many physical parameters of interest within physical systems or bodies can be measured by evaluating changes in the characteristics of energy waves or pulses. As one example, changes in the transit time or shape of an energy wave or pulse propagating through a changing medium can be measured to determine the forces acting on the medium and causing the changes. The propagation velocity of the energy waves or pulses in the medium is affected by physical changes in of the medium. The physical parameter or parameters of interest can include, but are not limited to, measurement of load, force, pressure, displacement, density, viscosity, and localized temperature. These parameters can be evaluated by measuring changes in the propagation time of energy pulses or waves relative to orientation, alignment, direction, or position as well as movement, rotation, or acceleration along an axis or combination of axes by wireless sensing modules or devices positioned on or within a body, instrument, equipment, or other mechanical system. Alternatively, measurements of interest can be taken using film sensors, mechanical sensors, polymer sensors, mems devices, strain gauge, piezo-resistive structure, and capacitive structures to name but a few.

Figure 2:
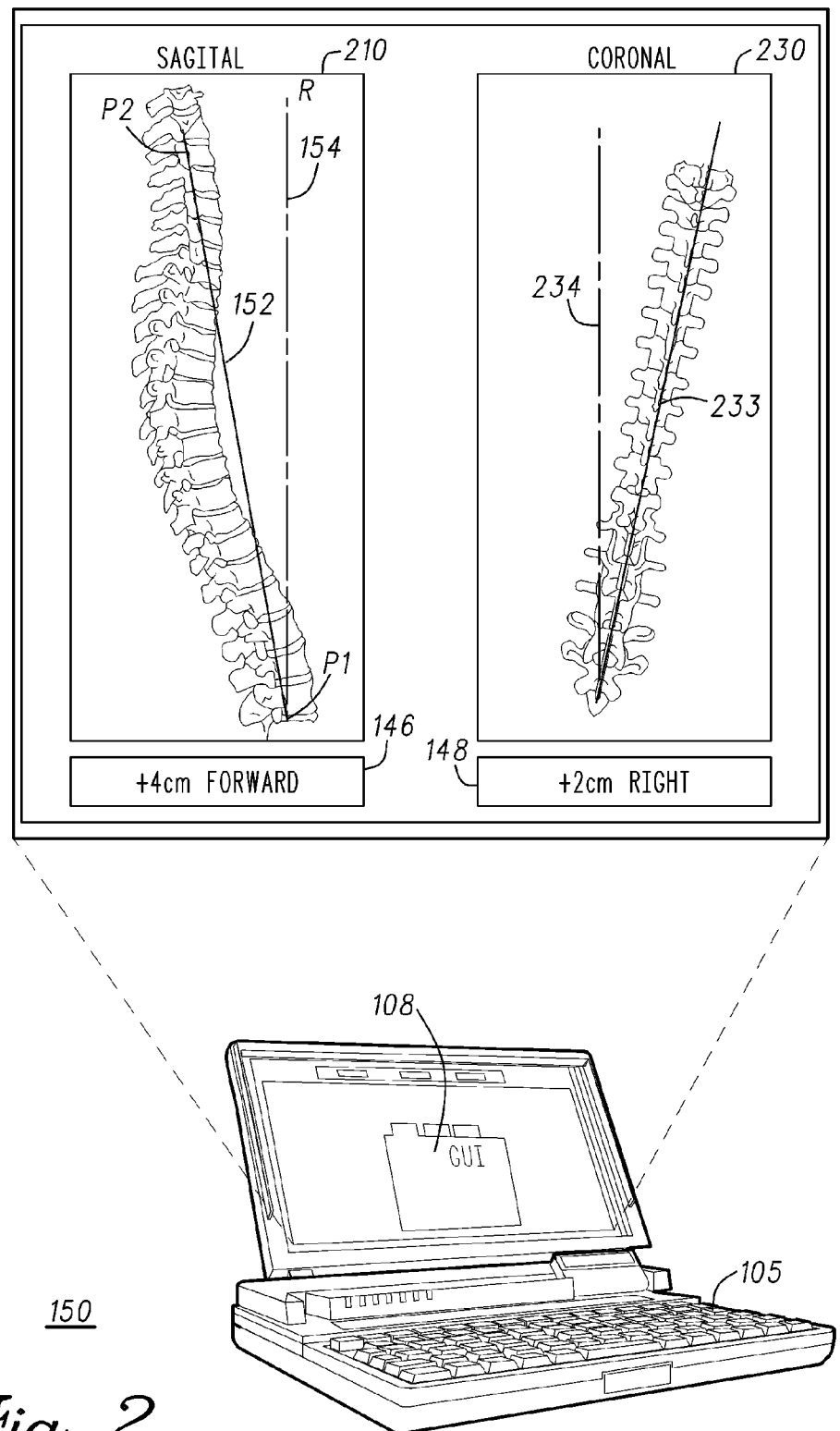
FIG. 2 illustrates a user interface showing spinal alignment and view projections in accordance with an example embodiment.

FIG. 2 illustrates a graphical user interface (GUI) 150 of the system 100 showing spinal alignment and view projections in a non-limiting example. The view projections provide three-dimensional visualization to the surgical procedure and system devices of FIG. 1 while displaying the quantitative measurements in real-time. Each view projection can be separately configured to show a different perspective of the spine with superimposed spine alignment information. The first view projection 210 shows a sagital view (i.e., front to back). The second view projection 230 shows a coronal view (i.e., side to side). The sagital and coronal views provide sufficient spatial information to visualize spine alignment with only two viewing projections. The view projections can be customized for different view angles and scene graphs.

As one example, the surgeon can hold the wand 103 and trace a contour of the spine, for instance, to determine the severity (or correction) of a scoliosis condition. This may be done prior to a surgery while the patient is standing to provide an indication of the patient's posture and spine curvature. The surgeon holds the wand and follows the contour of the spine. The GUI 108 visually shows the spinal contour from the positional information captured from the wand 103 during the trace. An alignment angle is then calculated from first order statistics and geometry (e.g., see angle points R, P1 and P2, where R is reference alignment, P1 is location of receiver 101, and P2 is point registered by wand 103). The alignment angle indicates the offset of the spinal alignment, and when projected in the view planes, shows the deviation error in the sagital and coronal planes. The GUI 108 can then report the required compensatory correction. In the current example, for instance, it reports a +4 cm forward required displacement in display box 146 to correct for sagital deviation of the angle between line 152 and line 154, and a +2 cm right required displacement in display box 148 to correct for coronal deviation of the angle between line 158 and line 156. This provides the surgeon with the minimal visual information to provide surgical alignment corrections.

Alternatively, a fast point-registration method can be employed to assess spinal alignment. The point registration method permits the surgeon to quickly assess spinal alignment with minimal registration. The user holds the wand and points and clicks on vertebra to create a point curve, which is converted to a line. In a first step A, the receiver 101 is positioned at a stationary location, for example, on a stand near the operating table. Alternatively, the receiver 101 can be rigidly pinned to the sacrum as shown in FIG. 1. In a second step B, the surgeon identifies three or more anatomical features on a reference bone with the wand 103 tip, such as points along the posterior iliac crest or dorsal surface on the sacrum. The system 100 determines the reference bone orientation from the registered wand tip spatial locations, for example, in a <x,y,z> Cartesian coordinate system relative to the receiver 101 origin. The system 100 then retrieves the associated 3D model spine components (e.g., sacrum, vertebra, etc.) from the image server 125, and displays them on the GUI 108 with the proper scaling and orientation (morphing and warping) in accordance with the reference bone orientation. Once the 3D model registration is complete, and while the patient remains stationary, the surgeon then registers one of the vertebrae, for example cervical vertebrae (C1-C7), in a third step C. The system 100 then has sufficient registered points to create a local coordinate system relative to the reference bone, generate a curve and line segment and report overall alignment as shown in FIG. 2. The spinal alignment is reported in view of a predetermined curvature or a straightness of the spine, for example, showing line 152 versus desired (pre-op planning) line 154.

Figure 3:
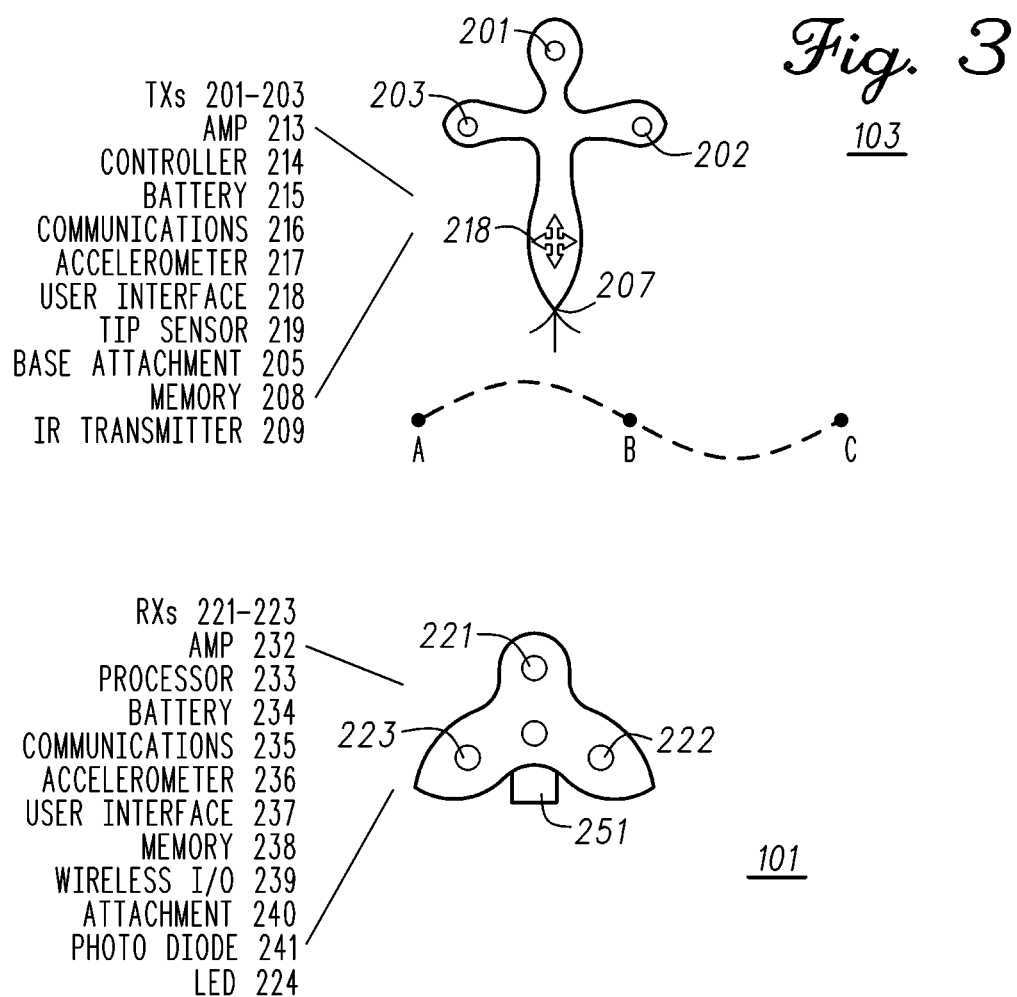
FIG. 3 illustrates the wand and the receiver of the spinal alignment system in accordance with an example embodiment.

FIG. 3 illustrates a non-limiting example of the wand 103 and the receiver 101, though, not all the components shown are required; fewer components can be used depending on required functionality. The receiver 101 and wand 103 and communication modes of operations there between are disclosed in U.S. patent application Ser. No. 12/900,662 entitled "Navigation Device Providing Sensory Feedback" filed Oct. 8, 2010; the entire contents of which are hereby incorporated by reference. Briefly, the current dimensions permit touchless tracking with sub millimeter spatial accuracy (<1 mm) up to approximately 2-m in distance. Either device and can be configured to support various functions (e.g., hand-held, mounted to object) and neither is limited to the dimensions described below.

The wand 103 is a hand-held device with a size dimension of approximately 10 cm in width, 2 cm depth, and an extendable length from 18 cm to 20 cm. As indicated above, the wand 103 can register points of interest (see points A, B, C), for example, along a contour of an object or surface, which can be shown in a user interface (see GUI 107 FIG. 1). As will be discussed ahead, the wand 103 and receiver 101 can communicate via ultrasonic, infrared and electromagnetic sensing to determine their relative location and orientation to one another. Other embodiments incorporating accelerometers provide further positional information.

The wand 103 includes sensors 201-203 and a wand tip 207. The sensors can be ultrasonic transducers, Micro Electro Mechanical Element (MEMS) microphones, electromagnets, optical elements (e.g., infrared, laser), metallic objects or other transducers for converting or conveying a physical movement to an electric signal such as a voltage or current. They may be active elements in that they are self-powered to transmit signals, or passive elements in that they are reflective or exhibit detectable magnetic properties.

In one embodiment, the wand 103 comprises three ultrasonic transmitters 201-203 each transmitting ultrasonic signals through the air, a controller (or electronic circuit) 214 for generating driver signals to the three ultrasonic transmitters 201-203 for generating the ultrasonic signals, an user interface 218 (e.g., button) that receives user input for performing short range positional measurement and alignment determination, a communications module 216 for relaying the user input and receiving timing information to control the electronic circuit 214, and a battery 218 for powering the electronic circuit 218 and associated electronics on the wand 103. The controller 214 is operatively coupled to the ultrasonic transmitters 201-203. Transmitters 201-203 transmit sensory signals in response to a directive by the controller 214. The wand 103 may contain more or less than the number of components shown; certain component functionalities may be shared as integrated devices.

Additional transmitter sensors can be included to provide an over-determined system for three-dimensional sensing. As one example, each ultrasonic transducer can perform separate transmit and receive functions. One such example of an ultrasonic sensor is disclosed in U.S. Pat. No. 7,725,288 the entire contents of which are hereby incorporated by reference. The ultrasonic sensors can transmit pulse shaped waveforms in accordance with physical characteristics of a customized transducer for constructing and shaping waveforms.

The wand tip 207 identifies points of interest on a structure, for example, an assembly, object, instrument or jig in three-dimensional space but is not limited to these. The tip does not require sensors since its spatial location in three-dimensional space is established by the three ultrasonic transmitters 201-203 arranged at the cross ends. However, a tip sensor 219 can be integrated on the tip 207 to provide ultrasound capabilities (e.g., structure boundaries, depth, etc.) or contact based sensing. In such case, the tip 207 can be touch sensitive to register points responsive to a physical action, for example, touching the tip to an anatomical or structural location. The tip can comprise a mechanical or actuated spring assembly for such purpose. In another arrangement it includes a capacitive touch tip or electrostatic assembly for registering touch. The wand tip 207 can include interchangeable, detachable or multi-headed stylus tips for permitting the wand tip to identify anatomical features while the transmitters 201-203 remain in line-of-sight with the receiver 101 (see FIG. 1). These stylus tips may be right angled, curved, or otherwise contoured in fashion of a pick to point to difficult to touch locations. This permits the wand to be held in the hand to identify via the tip 207, points of interest such as (anatomical) features on the structure, bone or jig.

The user interface 218 can include one or more buttons to permit handheld operation and use (e.g., on/off/reset button) and illumination elements to provide visual feedback. In one arrangement, an 8-state navigation press button 209 can communicate directives to further control or complement the user interface. It can be ergonomically located on a side of the wand to permit single-handed use. The wand 103 may further include a haptic module with the user interface 218. As an example, the haptic module may change (increase/decrease) vibration to signal improper or proper operation. The wand 103 includes material coverings for the transmitters 201-202 that are transparent to sound (e.g., ultrasound) and light (e.g., infrared) yet impervious to biological material such as water, blood or tissue. In one arrangement, a clear plastic membrane (or mesh) is stretched taught; it can vibrate under resonance with a transmitted frequency. The battery 218 can be charged via wireless energy charging (e.g., magnetic induction coils and super capacitors).

The wand 103 can include a base attachment mechanism 205 for coupling to a structure, object or a jig. As one example, the mechanism can be a magnetic assembly with a fixed insert (e.g., square post head) to permit temporary detachment. As another example, it can be a magnetic ball and joint socket with latched increments. As yet another example, it can be a screw post or pin to an orthopedic screw. Other embodiments may permit sliding, translation, rotation, angling and lock-in attachment and release, and coupling to standard jigs by way of existing notches, ridges or holes.

The wand 103 can further include an amplifier 213 and an accelerometer 217. The amplifier enhances the signal to noise ratio of transmitted or received signals. Accelerometer 217 identifies 3 and 6 axis tilt during motion and while stationary. Communications module 216 may include components (e.g., synchronous clocks, radio frequency 'RF' pulses, infrared 'IR' pulses, optical/acoustic pulse) for signaling to the receiver 101. The controller 214, can include a counter, a clock, or other analog or digital logic for controlling transmit and receive synchronization and sequencing of the sensor signals, accelerometer information, and other component data or status. The battery 218 powers the respective circuit logic and components. Infrared transmitter 209 pulses an infrared timing signal that can be synchronized with the transmitting of the ultrasonic signals (to the receiver).

Controller 214 can utilize computing technologies such as a microprocessor (uP) and/or digital signal processor (DSP) with associated storage memory 208 such as Flash, ROM, RAM, SRAM, DRAM or other like technologies for controlling operations of the aforementioned components of the device. The instructions may also reside, completely or at least partially, within other memory, and/or a processor during execution thereof by another processor or computer system. An Input/Output port permits portable exchange of information or data for example by way of Universal Serial Bus (USB). The electronic circuitry of the controller 214 can comprise one or more Application Specific Integrated Circuit (ASIC) chips or Field Programmable Gate Arrays (FPGAs), for example, specific to a core signal-processing algorithm. The controller 214 can be an embedded platform running one or more modules of an operating system (OS). In one arrangement, the storage memory may store one or more sets of instructions (e.g., software) embodying any one or more of the methodologies or functions described herein.

The receiver 101 comprises a processor 233 for generating timing information, registering a pointing location of the wand 103 responsive to the user input, and determining short range positional measurement and alignment from three or more pointing locations of the wand 103 with respect to the receiver 101. The receiver has size dimensions of approximately 2 cm width, 2 cm depth, and a length of 10 cm to 20 cm. It includes a communications module 235 for transmitting the timing information to the wand 103 that in response transmits the first, second and third ultrasonic signals. The ultrasonic signals can be pulse shaped signals generated from a combination of amplitude modulation, frequency modulation, and phase modulation. Three microphones 221-223 each receive the first, second and third pulse shaped signals transmitted through the air. Receiver 101 can be configured lineal or in more compact arrangements, it can comprise a triangular shape. One example of a device for three-dimensional sensing is disclosed in U.S. patent application Ser. No. 11/683,410 entitled "Method and Device for Three-Dimensional Sensing" filed Mar. 7, 2007 the entire contents of which are hereby incorporated by reference.

The memory 238 stores the ultrasonic signals and can produce a history of ultrasonic signals or processed signals. It can also store wand tip positions, for example, responsive to a user pressing the button to register a location. The wireless communication interface (Input/Output) 239 wirelessly conveys the positional information and the short-range alignment of the three or more pointing locations to a remote system. The remote system can be a computer, laptop or mobile device that displays the positional information and alignment information in real-time as described ahead. The battery powers the processor 233 and associated electronics on the receiver 101. The receiver 101 may contain more or less than the number of components shown; certain component functionalities may be shared or therein integrated.

Additional ultrasonic sensors can be included to provide an over-determined system for three-dimensional sensing. The ultrasonic sensors can be MEMS microphones, receivers, ultrasonic transmitters or combination thereof. As one example, each ultrasonic transducer can perform separate transmit and receive functions. One such example of an ultrasonic sensor is disclosed in U.S. Pat. No. 7,414,705 the entire contents of which are hereby incorporated by reference. The receiver 101 can also include an attachment mechanism 240 for coupling to bone or a jig by way of the pin 251. As one example, attachment mechanism 240 can be a magnetic assembly with a fixed insert (e.g., square post head) to permit temporary detachment. As another example, it can be a magnetic ball and joint socket with latched increments.

The receiver 101 can further include an amplifier 232, communications module 235, an accelerometer 236, and processor 233. The processor 233 can host software program modules such as a pulse shaper, a phase detector, a signal compressor, and other digital signal processor code utilities and packages. The amplifier 232 enhances the signal to noise of transmitted or received signals. The processor 233 can include a controller, counter, a clock, and other analog or digital logic for controlling transmit and receive synchronization and sequencing of the sensor signals, accelerometer information, and other component data or status. The accelerometer 236 can identify axial tilt (e.g., 3 and 6 axis) during motion and while stationary. The battery 234 powers the respective circuit logic and components. The receiver includes a photo diode 241 for detecting the infrared signal and establishing a transmit time of the ultrasonic signals to permit wireless infrared communication with the wand.

The communications module 235 can include components (e.g., synchronous clocks, radio frequency 'RF' pulses, infrared 'IR' pulses, optical/acoustic pulse) for local signaling (to wand 102). It can also include network and data components (e.g., Bluetooth, ZigBee, Wi-Fi, GPSK, FSK, USB, RS232, IR, etc.) for wireless communications with a remote device (e.g., laptop, computer, etc.). Although external communication via the network and data components is herein contemplated, it should be noted that the receiver 101 can include a user interface 237 to permit standalone operation. As one example, it can include 3 LED lights 224 to show three or more wand tip pointing location alignment status. The user interface 237 may also include a touch screen or other interface display with its own GUI for reporting positional information and alignment.

The processor 233 can utilize computing technologies such as a microprocessor (uP) and/or digital signal processor (DSP) with associated storage memory 238 such a Flash, ROM, RAM, SRAM, DRAM or other like technologies for controlling operations of the aforementioned components of the terminal device. The instructions may also reside, completely or at least partially, within other memory, and/or a processor during execution thereof by another processor or computer system. An Input/Output port permits portable exchange of information or data for example by way of Universal Serial Bus (USB). The electronic circuitry of the controller can comprise one or more Application Specific Integrated Circuit (ASIC) chips or Field Programmable Gate Arrays (FPGAs), for example, specific to a core signal processing algorithm or control logic. The processor can be an embedded platform running one or more modules of an operating system (OS). In one arrangement, the storage memory 238 may store one or more sets of instructions (e.g., software) embodying any one or more of the methodologies or functions described herein.

In a first arrangement, the receiver 101 is wired via a tethered electrical connection (e.g., wire) to the wand 103. That is, the communications port of the wand 103 is physically wired to the communications interface of the receiver 101 for receiving timing information. The timing information from the receiver 101 tells the wand 103 when to transmit and includes optional parameters that can be applied to pulse shaping. The processor 233 on the receiver 101 employs this timing information to establish Time of Flight measurements in the case of ultrasonic signaling with respect to a reference time base.

In a second arrangement, the receiver 101 is communicatively coupled to the wand 103 via a wireless signaling connection via wireless I/O 239. A signaling protocol is disclosed in U.S. patent application Ser. No. 12/900,662 entitled "Navigation Device Providing Sensory Feedback" filed Oct. 8, 2010; the entire contents of which are hereby incorporated by reference. An infrared transmitter 209 on the wand 103 transmits an infrared timing signal with each transmitted pulse shaped signal. It pulses an infrared timing signal that is synchronized with the transmitting of the ultrasonic signals to the receiver. The receiver 101 can include a photo diode 241 for determining when the infrared timing signal is received. In this case, the communications port of the wand 103 is wirelessly coupled to the communications interface of the receiver 101 by way of the infrared transmitter and the photo diode for relaying the timing information to within microsecond accuracy (~1 mm resolution). The processor 233 on the receiver 101 employs this infrared timing information to establish the first, second, and third Time of Flight measurements with respect to a reference transmit time.

Figure 4:
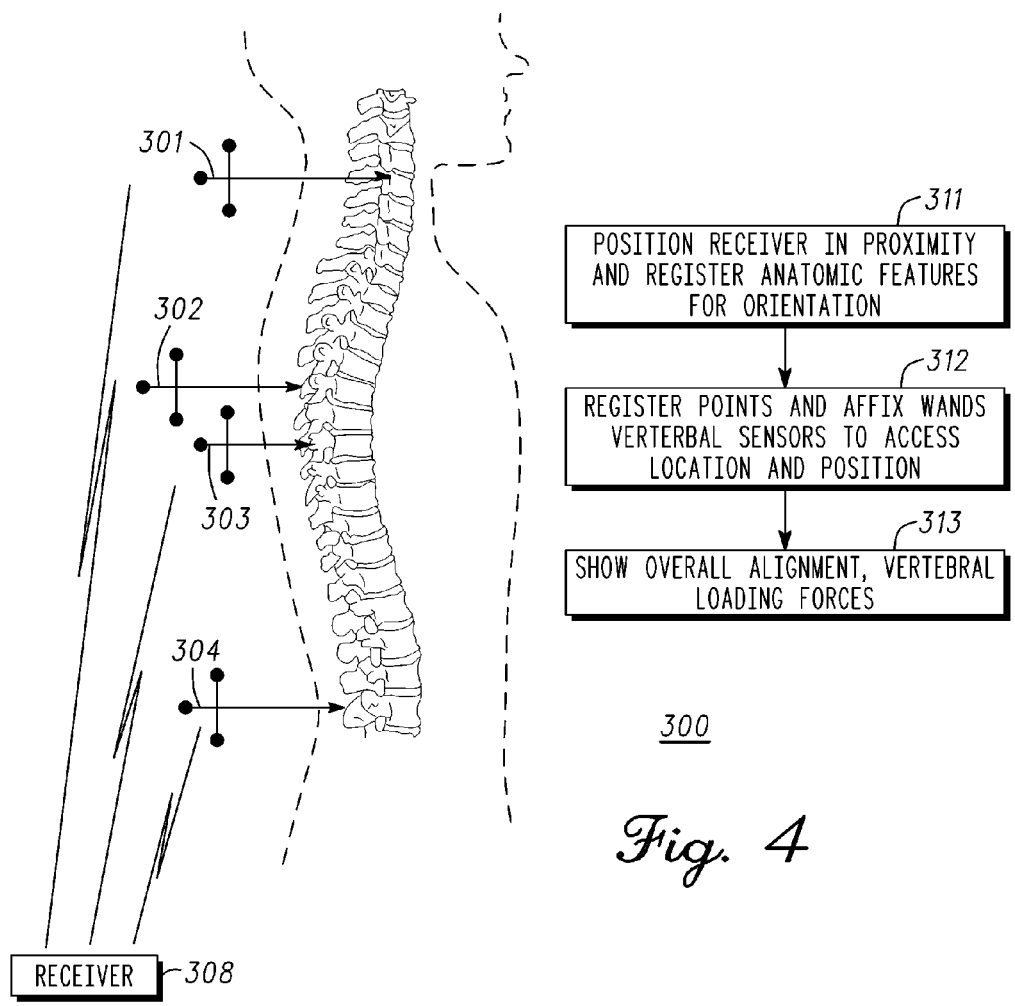
FIG. 4 illustrates multiple sensorized devices for determining spinal alignment in accordance with an example embodiment.

FIG. 4 illustrates multiple sensorized wands for evaluating spinal alignment 300 in a non-limiting example. As shown, multiple sensorized wands 301-304 can be employed to track individual vertebral movement and/or alignment relative to other tracked vertebrae. Each of the wands may be of a different size and sensor configuration. The wands are lightweight components that can span dimensions between 4 cm to 12 cm, and width of less than or equal to 1 cm. In general, the wands 301-304 have a form factor easily held by hand or can be attached and supported by the muscular-skeletal system. For example, a first wand 301 may have a wider and longer sensor span than another wand 303. This can enhance communication between the wands 301-304 and receiver 308. Each wand can have a separate ID to identify it from the others, for example, stored as a characteristic low frequency magnetic wavelength unique to the wand. The system 100 can identify the wands via the passive magnetic field and determine position via the one or more ultrasonic, optical, electromagnetic elements, or (passive/active) sensors.

In conjunction with the illustration of FIG. 4, a workflow method is herein contemplated. At a first workflow step 311, the receiver 308 is positioned in proximity to the surgical area and where the wands are expected to be used. As previously noted, the receiver 308 is placed on a stand or affixed to the sacrum (or other bony region) to track a wand's orientation and location. A wand may be held in a hand and used to register anatomic features on sacrum, for example, point and click the wand tip to a bone feature. This point registration captures anatomical points, which are then used to retrieve a 3D spine model with proper orientation and dimension. At step 312, the wand can then be used to register points on a vertebra to assess a location of that vertebra. In a first arrangement, the wand can be affixed to the vertebra directly without any wand tip point registration. This provides one point for assessing spatial location at the insertion point but not necessarily orientation (three-dimensional information).

In a second arrangement, the wand is first used to register points on the surface of the vertebra and then inserted therein. The registration captures anatomical vertebra points, which are then used to retrieve a 3D vertebra model with proper orientation and dimension. This permits the system 100 to track the vertebra with proper scaling and position when the wand is inserted therein. During the registration and positioning of the receiver on the sacrum and each wand on the vertebrae, the system 100 provides a real-time view of the instrument tracking as shown in step 313. That is, it produces a virtual environment showing the 3D model of the spine, sensorized wands 301-304 and receiver 308.

Figure 5:
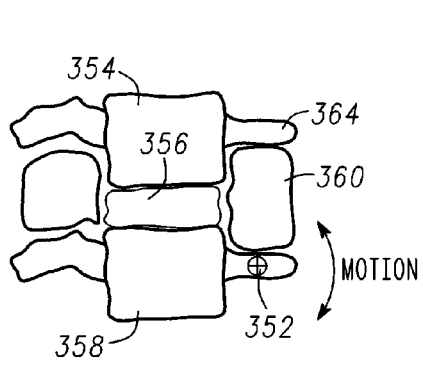
FIG. 5 illustrates sensorized placement for determining spinal parameters in accordance with an example embodiment.
Figure 6:
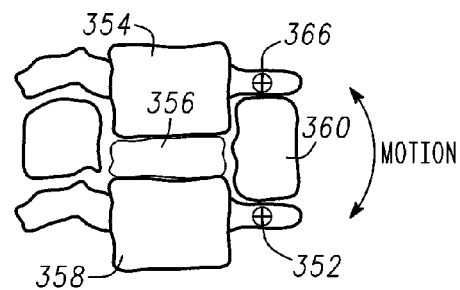
FIG. 6 illustrates placement of multiple sensors for determining spinal conditions in accordance with an example embodiment.

FIG. 5 illustrates sensorized placement for determining spinal conditions in a non-limiting example. As previously noted, the wand-tip may also include a sensor, such as a biometric transducer. The wand tip when used to register a point of interest can also capture biometric data directly related to the insertion site. The wand tip can also disengage the biometric transducer and leave it positioned at the site of contact. The illustrations of FIGS. 5 and 6 illustrate the placement of the wand tip sensor, which in some configurations deploys its tip sensor in-situ for long term implantation. The system 100 can also enable a transfer of energy waves in a vibratory pattern that can mimic load on the bone and lead to improved bone mineral content and density. The sensors can also send energy waves through or across an implant to, thus, aid in healing of a fracture.

Accordingly, a method is herein provided for detecting biometric parameters, which are a function of sensorized placement including position and orientation. The method includes providing a biometric transducer on a moving component of a vertebral joint, transmitting an energy wave (e.g., ultrasonic, optical, electromagnetic) from the biometric transducer into a procedure area different from the moving component of the vertebral joint during vertebral joint or spine motion, quantatively assessing the behavior of the energy wave during the vertebral joint motion; and based upon the assessed behavior and vertebral joint motion, determining a current status or at least one parameter of the procedure area selected from the group consisting of pressure, tension, shear, load, torque, bone density and bearing weight. Alternatively, an insertible head assembly incorporating one or more sensors can be used to measure the biometric parameter of interest. In the example, the biometric transducer can detect and transmit information regarding motion and loads of vertebra. As one example, the sensors can detects abnormal motion of the orthopedic joint by evaluating a frequency or periodicity of the assessed behavior, for example, as the vertebral joint is flexed during movement.

As one example shown in FIG. 5, a single sensor 352 can be implanted on a bone or prosthetic component of the vertebral joint (e.g., vertebra) to assess behavior of the vertebral joint during movement, such as, a quality or functionality of the joint mechanics as related to pressure, tension, shear, bone density and bearing weight. The sensor 352 in this embodiment is at a fixed location on the bone (vertebra) and moves with the vertebra 358 during motion relative to the procedure area 360. As shown, the procedure area 360 comprises vertebra 354, disc 356, and vertebra 358. The procedure area 360 is relatively stationary with respect to the sensor since the vertebra primarily moves the single sensor. The single sensor in this arrangement is exposed to various changes in the parameter of interest (e.g., pressure, tension, shear, bone density, and bearing weight) in the procedure area as a result of the motion. As one example, the sensor is compressed through the range of joint movement consequent to actions applied at different locations in the joint during the motion. During motion, sensor 352 assesses the energy waves in the procedural area; an adjacent area is also assessed because the movement of the vertebra (and accordingly the sensor focus) changes with respect to the procedure area as a result of the motion. The position of sensor 352 (by way of the wand when attached thereto) is also determined in relation to the other vertebra and used to catalog changes in the sensed parameter with respect to orientation, location and position.

One advantage of placing sensor 352 on a moving component (e.g., vertebra, prosthetic implant) and transmitting an energy wave into a procedure area different from the moving component of the vertebral joint, with knowledge of its location and orientation, is that it effectively changes the distance between sensor 352 and the procedure area which changes the resolution and focus of sensor 352 as well as forces thereon. The positional information also indicates periodicity of movement as related to changes in the sensed parameter. As one example, sensor 352 operating in a switched transmit and receive mode can take measurements at different depths of the procedure area without incurring operational changes. Sensor 352 as a result of the changing distance due to joint movement, can take different measurements without sensor adjustment that could otherwise require changing a frequency, amplitude, or phase of the transmitted energy wave, for example, to match impedances.

As one example, biometric sensor 352 can be an ultrasound device. Quantitative ultrasound, in contrast to other bone-densitometry methods that measure only bone-mineral content, can measure additional properties of bone such as mechanical integrity. Propagation of the ultrasound wave through bone is affected by bone mass, bone architecture, and the directionality of loading. Quantitative ultrasound measurements as measures for assessing the strength and stiffness of bone are based on the processing of the received ultrasound signals. The speed of sound and the ultrasound wave propagates through the bone and the soft tissue. Prosthetic loosening or subsidence, and fracture of the femur/tibia/acetabulum or the prosthesis, are associated with bone loss. Consequently, an accurate assessment of progressive quantifiable changes in periprosthetic bone-mineral content may help the treating surgeon to determine when to intervene in order to preserve bone stock for revision arthroplasty. This information helps in the development of implants for osteoporotic bone, and aids in the evaluation of medical treatment of osteoporoses and the effects of different implant coatings.

FIG. 6 illustrates multiple sensorized placements for determining spinal conditions in a non-limiting example. As previously noted, the wand-tip may also include a sensor, such as a biometric transducer. The wand tip when used to register a point of interest can also capture biometric data directly related to the insertion site. The wand tip can also disengage the biometric transducer and leave it positioned at the site of contact.

Accordingly, a method is herein provided for detecting biometric parameters comprising providing a second biometric transducer at the procedure area that is different from the moving component of the vertebral joint, and quantatively assessing the behavior of the energy wave based on a relative separation of the first biometric transducer and second biometric transducer during the vertebral joint motion. A current status or at least one parameter of the procedure area is determined from the assessed behavior and vertebral joint motion. The parameter is one of strain, vibration, kinematics, and stability. A first biometric transducer or the second biometric transducer can include a transceiver for transmitting data relating to the at least one biometric parameter to an external source for assessment.

As shown in FIG. 6 sensor 352 can be implanted on a bone or prosthetic component of an vertebral joint (e.g., vertebra) and a sensor 366 can be positioned at a different position in the procedure area for assessing behavior of the vertebral joint during movement. Sensor 352 in this embodiment is at a fixed location on the bone (vertebra) and moves with the vertebra during joint motion relative to sensor 366 in the procedure area. The sensor 366 can be on a different bone. Although both sensors can move, sensor 352 in effect can be considered moving relative to sensor 366 and is relatively displaced as indicated. The sensors 352 and 366 allow evaluation of the host bone and tissue regarding, but not limited to bone density, fluid viscosity, temperature, strain, pressure, angular deformity, vibration, load, torque, distance, tilt, shape, elasticity, motion, and others.

The dual sensor arrangement shown can evaluate of bone integrity. For instance, in a vertebral joint, sensors 352 and 366 coupled to a first and second vertebra assess the bone density. External and internal energy waves sent by sensor 352, sensor 366, or both according to the invention can be used during the treatment of fractures and spinal fusions. With two deployed sensors, the distance between the sensors can be determined at the area of concern and the power field that can be generated. The energy fields can be standard energy sources such as ultrasound, radiofrequency, and/or electromagnetic fields. The deflection of the energy wave over time, for example, will allow the detection of changes in the desired parameter that is being evaluated. As an example, a first sensor placed on a distal end of the femur bone can assess bone density from a second sensor embedded on a proximal end of the tibia bone during vertebral movement.

One advantage of two or more sensors is that they move closer and farther apart relative to one another as a result of the motion; actions that improve an assessment of the energy wave, for example, due to the frequency characteristics of the sensors and impedance characteristics of the procedure area under investigation. Again, the relative separation of sensors 352 and 366 may permit taking different measurements without sensor adjustment that could otherwise require changing a frequency, amplitude, or phase of the transmitted energy wave, for example, to match impedances. In the current example, the measurement of bone is based on the processing of the received ultrasound signals. Speed of the sound and the ultrasound velocity both provide measurements on the basis of how rapidly the ultrasound wave propagates through the bone and the soft tissue. These measures characteristics permit creation of a rapid three-dimensional geometry, which information can be processed by the system 100 in conjunction with positional, orientation and location information. Because the sensors span a joint space, they can detect changes in the implant function. Examples of implant functions include bearing wear, subsidence, bone integration, normal and abnormal motion, heat, change in viscosity, particulate matter, kinematics, to name a few.

Figure 7:
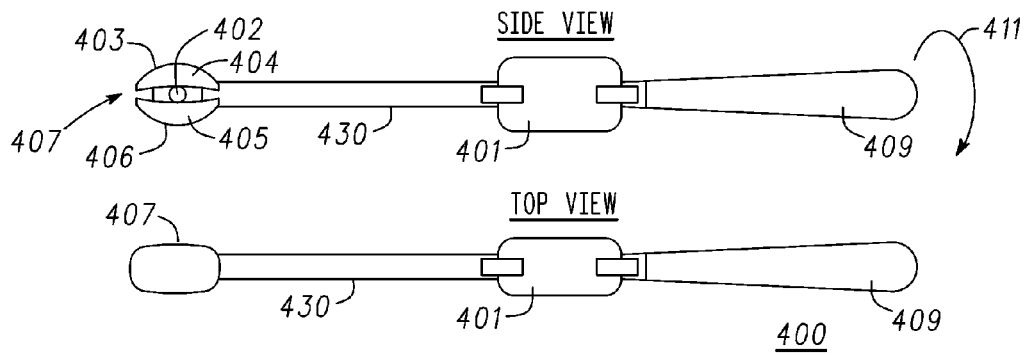
FIG. 7 illustrates a sensorized spinal instrument in accordance with an example embodiment.

FIG. 7 illustrates a sensorized spinal instrument 400 in a non-limiting example. A side view and a top view are presented. Spinal instrument 400 comprises a handle 409, a shaft 430, and a sensored head 407. The handle 409 is coupled at a proximal end of the shaft 430 and the sensored head 407 is coupled to a distal end of the shaft 430. In one embodiment, handle 409, shaft 430, and sensored head 407 form a rigid structure that does not flex when used to distract or measure a spinal region. Spinal instrument 400 includes an electronic assembly 401 operatively coupled to one or more sensors in sensored head 407. The sensors are coupled to surfaces 403/406 on moving components 404/405 of sensored head 407. The electronic assembly 401 is located towards the proximal end of the shaft 407 or in handle 409. As shown, the electronic assembly 401 is coupled to shaft 409. Electronic assembly 401 comprises electronic circuitry that includes logic circuitry, an accelerometer, and communication circuitry. In one embodiment, surfaces 403 and 406 of sensored head 407 can have a convex shape. The convex shape of surfaces 403 and 406 support placement of sensored head 407 within the spinal region and more specifically between the contours of vertebrae. In one embodiment, sensored head 407 is height adjustable by way of the top component 404 and the bottom component 405 through a jack 402 that evenly distracts and closes according to handle 409 turning motion 411. Jack 402 is coupled to interior surfaces of components 404 and 405 of sensored head 407. Shaft 430 includes one or more lengthwise passages. For example, interconnect such as a flexible wire interconnect can couple through one lengthwise passage of shaft 430 such that electronic assembly 401 is operatively coupled to one or more sensors in sensored head 407. Similarly, a threaded rod can couple through a second passage of shaft 430 for coupling handle 409 to jack 404 thereby allowing height adjustment of sensored head 407 via rotation of handle 409.

Spine instrument 400 can also determine an orientation by way of embedded accelerometers. The sensored head 407 supports multiple functions that include the ability to determine a parameter of the procedure area (e.g., intervertebral space) including pressure, tension, shear, load, torque, bone density, and/or bearing weight. In one embodiment, more than one load sensor can be included within sensored head 407. The more than one load sensors can be coupled to predetermined locations of surfaces 403 and 406. Having more than one load sensor allows the sensored head 407 to measure load magnitude and the position of applied load to surfaces 403 and 406. The sensored head 407 can be used to measure, adjust, and test a vertebral joint prior to installing a vertebral component. As will be seen ahead, the alignment system 100 evaluates the optimal insertion angle and position of the spine instrument 400 during intervertebral load sensing and replicates these conditions when using an insert instrument.

In the present invention these parameters can be measured with an integrated wireless sensored head 407 or device comprising an i) encapsulating structure that supports sensors and contacting surfaces and ii) an electronic assemblage that integrates a power supply, sensing elements, ultrasound resonator or resonators or transducer or transducers and ultrasound waveguide or waveguides, biasing spring or springs or other form of elastic members, an accelerometer, antennas and electronic circuitry that processes measurement data as well as controls all operations of energy conversion, propagation, and detection and wireless communications. The sensored head 407 or instrument 400 can be positioned on or within, or engaged with, or attached or affixed to or within, a wide range of physical systems including, but not limited to instruments, appliances, vehicles, equipments, or other physical systems as well as animal and human bodies, for sensing and communicating parameters of interest in real time.

An example of using the spinal instrument 400 is in the installation of a spinal cage. The spinal cage is used to space vertebrae in replacement of a disc. The spinal cage is typically hollow and can be formed having threads for fixation. Two or more cages are often installed between the vertebrae to provide sufficient support and distribution of loading over the range of motion. In one embodiment, the spinal cage is made titanium for lightweight and strength. A bone growth material can also be placed in the cage to initiate and promote bone growth thereby further strengthening the intervertebral area long-term. The spinal instrument 400 is inserted in the gap between vertebrae to measure load and position of load. The position of load corresponds to the vertebral area or surfaces applying the load on the surfaces 403 or 406 of sensored head 407. The angle and position of insertion of the sensored head 407 of spinal instrument 400 can also be measured. The load magnitude and position of load measurement are used by the surgeon to determine an implant location between the vertebrae and the optimal size of the spinal cage for the implant location. The optimal size will be a cage height that when loaded by the spine falls within a predetermined load range. Typically, the height of sensored head 407 used to distract and measure force applied by the vertebrae of interest is equal to the cage height implanted in a subsequent step. After removing the sensored head 407 from the vertebrae the spinal cage can be implanted in the same region. The loading on the implanted spinal cage is approximately equal to the measurements made by spinal instrument 400 and applied to sensor head 407. In one embodiment, the angle and position of the insertion trial measurement is recorded by spinal instrument 400 or a remote system coupled thereto. The angle and position measurements are subsequently used to guide the spinal cage into the same region of the spine in an identical path as spinal instrument 400 during a measurement process.

Figure 8:
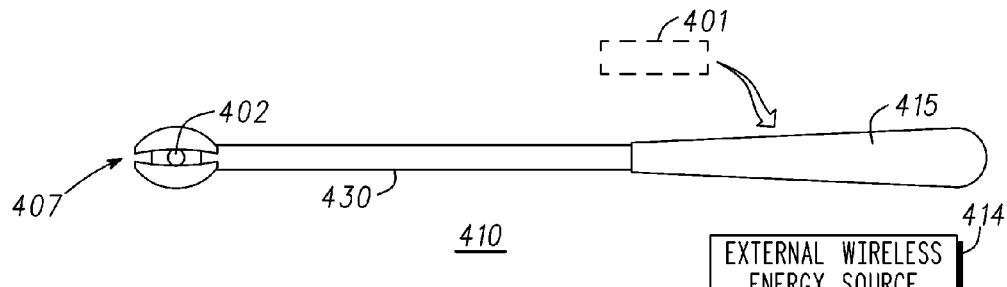
FIG. 8 illustrates an integrated sensorized spinal instrument in accordance with an example embodiment.

FIG. 8 illustrates an integrated sensorized spinal instrument 410 in a non-limiting example. In particular, the electronic assembly 401 is internal to the integrated instrument 410. It includes an external wireless energy source 414 that can be placed in proximity to a charging unit to initiate a wireless power recharging operation. The wireless energy source 414 can include a power supply, a modulation circuit, and a data input. The power supply can be a battery, a charging device, a capacitor, a power connection, or other energy source for generating wireless power signals that can transfer power to spinal instrument 410. The external wireless energy source 414 can transmit energy in the form of, but not limited to, electromagnetic induction, or other electromagnetic or ultrasound emissions. In at least one exemplary embodiment, the wireless energy source includes a coil to electromagnetically couple and activate (e.g., power on) with an induction coil in sensing device when placed in close proximity.

The electronic assembly 401 transmits measured parameter data to a receiver via data communications circuitry for permitting visualization of the level and distribution of the parameter at various points on the vertebral components. The data input can also be an interface or port to receive the input information from another data source, such as from a computer via a wired or wireless connection (e.g., USB, IEEE802.16, etc.). The modulation circuitry can modulate the input information onto the power signals generated by the power supply. Sensored head 407 has wear surfaces that are typically made of a low friction polymer material. Ideally, the sensored head 407 when inserted between vertebrae has an appropriate loading, alignment, and balance similar that is similar to a natural spine.

Figure 9:
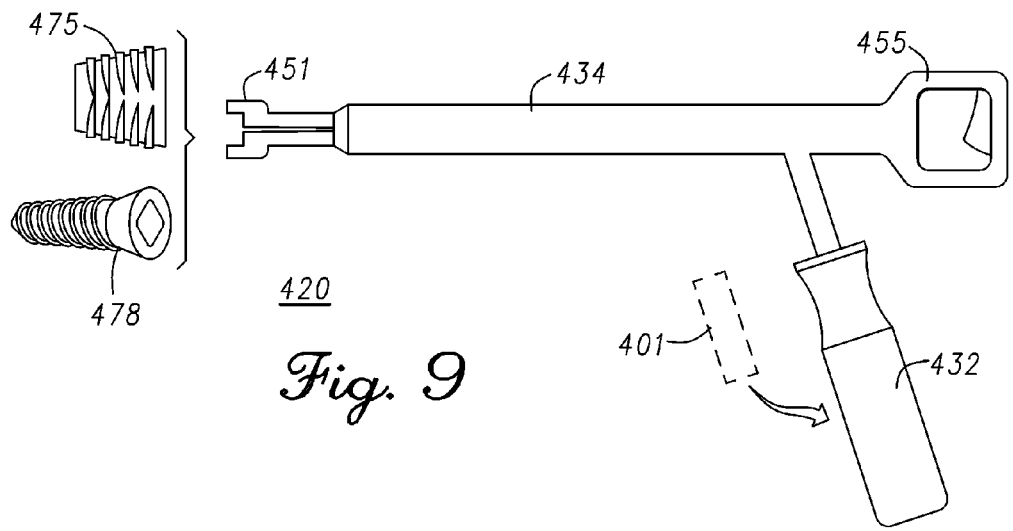
FIG. 9 illustrates an insert instrument with vertebral components in a non-limiting example.

FIG. 9 illustrates an insert instrument 420 with vertebral components in a non-limiting example. Electronic assembly 401 as described herein similarly supports the generation of orientation and position data of insert instrument 420. By way of the alignment system 100, the user can replicate the insertion angle, position and trajectory (path) to achieve proper or pre-planned placement of the vertebral component. Alternatively, an accelerometer in electronic assembly 401 can provide location and trajectory information. Insert instrument 420 comprises a handle 432, a neck 434, and a tip 451. An attach/release mechanism 455 couples to the proximal end of neck 434 for controlling tip 451. Attach/release mechanism 455 allows a surgeon to retain or release vertebral components coupled to tip 451. In the example, handle 432 extends at an angle in proximity to a proximal end of neck 434. Positioning of handle 432 allows the surgeon to accurately direct tip 451 in a spinal region while allowing access to attach/release mechanism 455.

In a first example, the vertebral component is a spine cage 475. The spine cage 475 is a small hollow cylindrical device, usually made of titanium, with perforated walls that can be inserted between the vertebrae of the spine during a surgery. In general, a distraction process spaces the vertebrae to a predetermined distance prior insertion of spine cage 475. Spine cage 475 can increase stability, decrease vertebral compression, and reduce nerve impingement as a solution to improve patient comfort. Spine cage 475 can include surface threads that allow the cage to be self-tapping and provide further stability. Spine cage 475 can be porous to include bone graft material that supports bone growth between vertebral bodies through cage 475. More than one spine cage can be placed between vertebrae to alleviate discomfort. Proper placement and positioning of spine cage 475 is important for successful long-term implantation and patient outcome.

In a second example, the vertebral component is a pedicle screw 478. The pedicle screw 478 is a particular type of bone screw designed for implantation into a vertebral pedicle. There are two pedicles per vertebra that couple to other structures (e.g. lamina, vertebral arch). A polyaxial pedicle screw may be made of titanium to resist corrosion and increase component strength. The pedicle screw length ranges from 30 mm to 60 mm. The diameter ranges from 5.0 mm to 8.5 mm. It is not limited to these dimensions, which serve as dimensional examples. Pedicle screw 478 can be used in instrumentation procedures to affix rods and plates to the spine to correct deformity, and/or treat trauma. It can be used to immobilize part of the spine to assist fusion by holding bony structures together. By way of electronic assembly 401 (which may be internally or externally integrated), the insert instrument 420 can determine depth and angle for screw placement and guide the screw therein. In the example, one or more accelerometers are used to provide orientation, rotation, angle, or position information of tip 451 during an insertion process.

In one arrangement, the screw 478 is embedded with sensors. The sensors can transmit energy and obtain a density reading and monitor the change in density over time. As one example, the system 100 can thus monitor and report healing of a fracture site. The sensors can detect the change in motion at the fracture site as well as the motion between the screw and bone. Such information aids in monitoring healing and gives the healthcare provider an ability to monitor vertebral weight bearing as indicated. The sensors can also be activated externally to send energy waves to the fracture itself to aid in healing.

Figure 10:
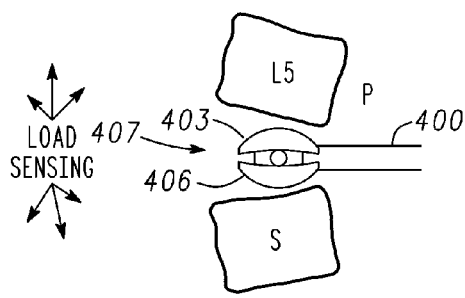
FIG. 10 illustrates the spinal instrument positioned between vertebra of the spine for parameter sensing in accordance with an example embodiment.

FIG. 10 illustrates a perspective view of the spinal instrument 400 positioned between vertebrae of the spine for sensing vertebral parameters in a non-limiting example. In general, a compressive force is applied to surfaces 403 and 406 when sensored head 407 is inserted into the spinal region. In one embodiment, sensored head 407 includes two or more load sensors that identify magnitude vectors of loading on surface 403, surface 406, or both associated with inter-vertebral force there between. In the example shown, the spinal instrument 400 is positioned between vertebra (L5) and the Sacrum (S) such that a compressive force is applied to surfaces 403 and 406. One approach for inserting the instrument 400 is from the posterior (back side) through a minilaparotomy as an endoscopic approach may be difficult to visualize or provide good exposure. Another approach is from the anterior (front side) which allows the surgeon to work through the abdomen to reach the spine. In this way spine muscles located in the back are not damaged or cut; avoiding muscle weakness and scarring. Spinal instrument 400 can be used with either the anterior or posterior spine approach.

Aspects of the sensorized components of the spine instrument 400 are disclosed in U.S. patent application Ser. No. 12/825,638 entitled "System and Method for Orthopedic Load Sensing Insert Device" filed Jun. 29, 2010, and U.S. patent application Ser. No. 12/825,724 entitled "Wireless Sensing Module for Sensing a Parameter of the Muscular-Skeletal System" filed Jun. 29, 2010 the entire contents of which are hereby incorporated by reference. Briefly, the sensored head 407 can measure forces (Fx, Fy, and Fz) with corresponding locations and torques (e.g. Tx, Ty, and Tz) and edge loading of vertebrae. The electronic circuitry 401 (not shown) controls operation and measurements of the sensors in sensored head 407. The electronic circuitry 401 further includes communication circuitry for short-range data transmission. It can then transmit the measured data to the remote system to provide real-time visualization for assisting the surgeon in identifying any adjustments needed to achieve optimal joint balancing.

A method of installing a component in the muscular-system is disclosed below. The steps of the method can be performed in any order. An example of placing a cage between vertebrae is used to demonstrate the method but the method is applicable to other muscular-skeletal regions such as the knee, hip, ankle, spine, shoulder, hand, arm, and foot. In a first step, a sensored head of a predetermined width is placed in a region of the muscular-skeletal system. In the example, the insertion region is between vertebrae of the spine. A hammer can be used to tap an end of the handle to provide sufficient force to insert the sensored head between the vertebrae. The insertion process can also distract the vertebrae thereby increasing a separation distance. In a second step, the position of the load applied to the sensored head is measured. Thus, the load magnitude and the position of the loading on the surfaces of the sensored head are available. How the load applied by the muscular-skeletal system is positioned on the surfaces of the sensored head can aid in determining stability of the component once inserted. An irregular loading applied to sensored head can predict a scenario where the applied forces thrust the component away from the inserted position. In general, the sensored head is used to identify a suitable location for insertion of the component based on quantitative data. In a third step, the load and position of load data from the sensored head is displayed on a remote system in real-time. Similarly, in a fourth step, the at least one of orientation, rotation, angle, or position is displayed on the remote system in real-time. Changes made in positioning the sensored head are reflected in data on the remote system display. In a fifth step, a location between vertebrae having appropriate loading and position is identified and the corresponding quantitative measurement data is stored in memory.

In a sixth step, the sensored head is removed. In a seventh step, the component is inserted in the muscular-skeletal system. As an example, the stored quantitative measurement data is used to support the positioning of the component in the muscular-skeletal system. In the example, the insertion instrument can be used to direct the component into the muscular-skeletal system. The insertion instrument is an active device providing orientation, rotation, angle, or position of the component as it is being inserted. The previously measured direction and location of the insertion of the sensored head can be used to guide the insertion instrument. In one embodiment, the remote system display can aid in displaying relational alignment of the insertion instrument and component to the previously inserted sensored head. The insertion instrument in conjunction with the system can provide visual, vocal, haptic or other feedback to further aid in directing the placement of the component. In general, the component being inserted has substantially equal height as the sensored head. Ideally, the component is inserted identical in location and position to the previously inserted sensored head such that the loading and position of load on the component is similar to the quantitative measurements. In an eighth step, the component is positioned identically to the previously inserted sensored head and released. The insertion instrument can then be removed from the muscular-skeletal system. In a ninth step, at least the sensored head is disposed of.

Thus, the sensored head is used to identify a suitable location for insertion of the component. The insertion is supported by quantitative measurements that include position and location. Furthermore, the approximate loading and position of loading on the component is known after the procedure has been completed. In general, knowing the load applied by the muscular-skeletal system and the position on the surfaces of the component can aid in determining stability of the component long-term. An irregular loading applied on the component can result in the applied forces thrusting the component away from the inserted position.

Figure 11:
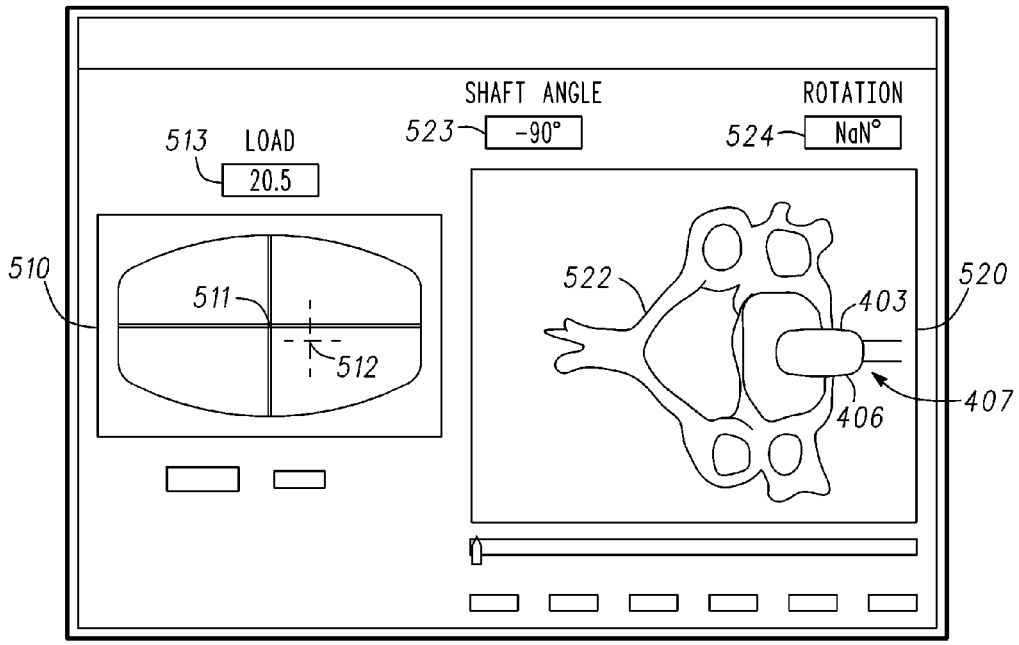
FIG. 11 illustrates a user interface showing a perspective view of the sensorized spinal instrument of FIG. 10 in accordance with an example embodiment.

FIG. 11 illustrates a graphical user interface (GUI) 500 showing a perspective view of the sensorized spinal instrument of FIG. 10 in a non-limiting example. The user interface 500 is presented by way of the remote system 105 and alignment system 100 (see FIG. 1). The GUI 500 includes a window 510 and a related window 520. The window 520 shows the spine instrument 400 and sensor head 407 in relation to a vertebra 522 under evaluation. In this example, a perspective (top) view of the vertebra is shown. It indicates a shaft angle 523 and a rotation component 524 which reveal the approach angle and rotation of the spine instrument 400, for instance, as it is moved forward into the incision. The window 520 and corresponding GUI information is presented and updated in real-time during the procedure. It permits the surgeon to visualize use of the spine instrument 400 and the sensed parameters. The window 510 shows a sensing surface (403 or 406) of the sensored head 407. A cross hair 512 is superimposed on the sensor head image to identify the maximal point of force and location. It can also lengthen to show vertebral edge loading. A window 513 reports the load force, for example, 20 lbs across the sensor head surface. This information is presented and updated in real-time during the procedure.

As previously noted, the system 100 can be used intra-operatively to aid in the implantation of the prosthesis/instrumentation/hardware by way of parameter sensing (e.g., vertebral load, edge loading, compression, etc.). The components such as receiver 101, plurality of wands 103, and spinal instrument 400 remain within the surgical field when used. The remote system 105 is typically outside the surgical field. All measurements are made within the surgical field by these components. In one embodiment, at least one of the receiver 101, plurality of wands 103, and spinal instrument are disposed of after the procedure is completed. In general, they are designed to be powered for a single use and cannot be re-sterilized.

In the spine, the affects on the bony and soft tissue elements are evaluated by the system 100, as well as the soft tissue (e.g., cartilage, tendon, ligament) changes during surgery, including corrective spine surgery. The sensors are then used during the operation (and post-operatively) to evaluate and visualize changes over time and dynamic changes. The sensors can be activated intra-operatively when surgical parameter readings are stored. Immediately post-operatively, the sensor is activated and a baseline is known.

The sensor system 100 allows evaluation of the spine and connective tissue regarding, but not limited to bone density, fluid viscosity, temperature, strain, pressure, angular deformity, vibration, load, torque, distance, tilt, shape, elasticity, and motion. Because the sensors span a vertebral space, they can predict changes in the vertebral component function prior to their insertion. As previously noted, the system 100 is used to place the spine instrument 400 in the intervertebral space, where it is shown positioned relative to the vertebral body 522. Once it is placed and visually confirmed in the vertebral center, the system 100 reports any edge loading on the instrument which in turn is used to size a proper vertebral device and insertion plan (e.g., approach angle, rotation, depth, path trajectory). Examples of implant component function include bearing wear, subsidence, bone integration, normal and abnormal motion, heat, change in viscosity, particulate matter, kinematics, to name a few.

Figure 12:
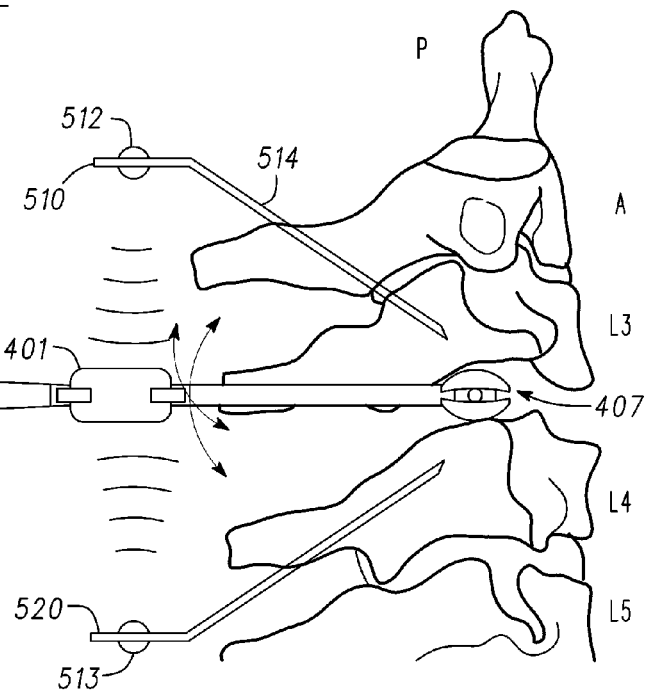
FIG. 12 illustrates the sensorized spinal instrument positioned between vertebra of the spine for intervertebral position and force sensing in accordance with an example embodiment.

FIG. 12 illustrates the sensorized spinal instrument 400 positioned between vertebra of the spine for intervertebral position and force sensing in a non-limiting example. As shown, sensed head 407 of spinal instrument 400 is placed between vertebrae a L4 and L5 vertebrae. The spinal instrument 400 distracts the L4 and L5 vertebrae the height of sensored head 407 and provides quantitative data on load magnitude and position of load. In one embodiment, spinal instrument 400 communicates with a first wand 510 and a second wand 520 positioned adjacent on each side thereof. A long shaft 514 is provided on each wand to permit placement within vertebra of the spine and also line up with other wands and an electronic assembly 401 of the spine instrument 400. Wand 510 tracks an orientation and position of vertebra L4, while wand 520 tracks an orientation and position of vertebra L5. This permits the system 100 to track an orientation and movement of the spine instrument 400 relative to movement of the neighboring vertebra. Each wand is sensorized similar to the spine instrument 400. Wand 510 and wand 520 respectively includes a sensor 512 and a sensor 513. Sensors 512 and 513 can transmit and receive positional information. The electronic assembly 401 in conjunction with wands 510 and 520 dually serves to resolve an orientation and position of the spine instrument 400 during the procedure. One example of an ultrasonic positional sensing is disclosed in U.S. patent application Ser. No. 12/764,072 entitled "Method and System for Positional Measurement" filed Apr. 20, 2010 the entire contents of which are hereby incorporated by reference.

Figure 13:
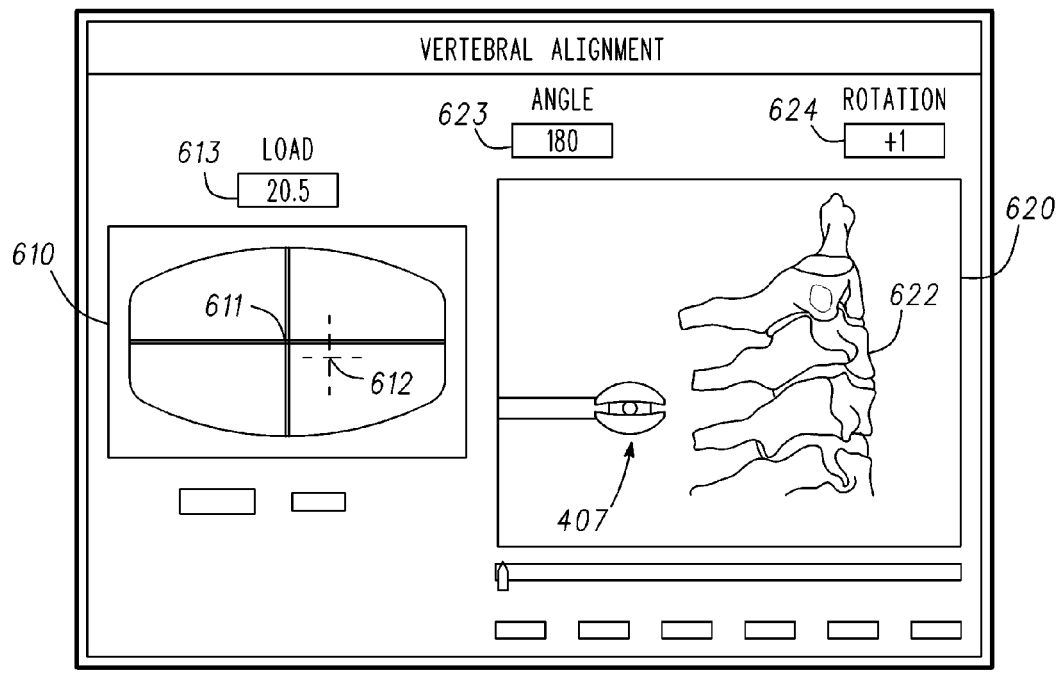
FIG. 13 illustrates a perspective view of a user interface showing the sensorized spinal instrument of FIG. 12 in accordance with an example embodiment.

FIG. 13 illustrates a perspective view of a user interface 600 showing the sensorized spinal instrument of FIG. 12 in a non-limiting example. User interface 600 is presented by way of the remote system 105 and alignment system 100 (see FIG. 1). The GUI 600 includes a first window 610 and a related second window 620. The second window 620 shows the spine instrument and sensored head 407 in relation to a vertebral component 622 under evaluation. In this example, a sagital (side) view of the spine column is shown. It indicates a shaft angle 623 and a rotation component 624 which reveal the approach angle and rotation of the spine instrument and sensored head 407. The second window 620 and corresponding GUI information is presented and updated in real-time during the procedure. It permits the surgeon to visualize the sensored head 407 of the spinal instrument 400 and the sensed load force parameters. The first window 610 shows a sensing surface of the sensor head (see FIG. 7). A cross hair 612 is superimposed on the image of sensored head 407 to identify the maximal point of force and location. It can also adjust in width and length to show vertebral edge loading. Another GUI window 613 reports the load force across the sensored head 407 surface. The GUI 600 is presented and updated in real-time during the procedure.

Figure 14:
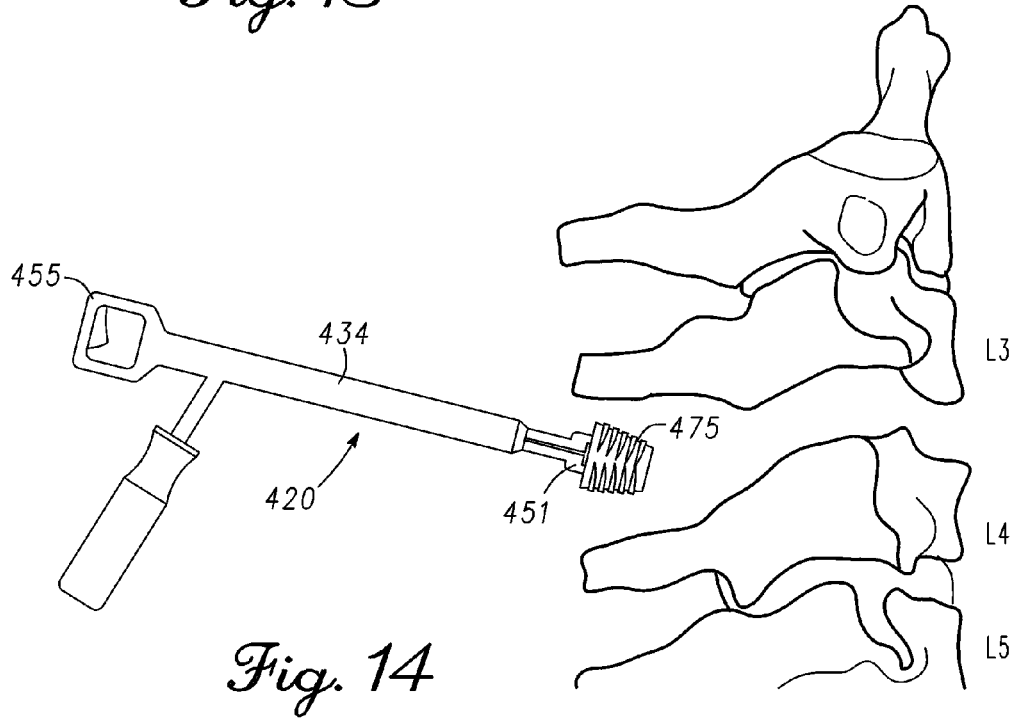
FIG. 14 illustrates the sensorized spinal insert instrument for placement of a spine cage in accordance with an example embodiment.

FIG. 14 illustrates a perspective view of sensorized spinal insert instrument 420 for placement of spine cage 475 in a non-limiting example. Insert instrument 420 provides a surgical means for implanting vertebral component 475 (e.g. spine cage, pedicle screw, sensor) between the L4 and L5 vertebrae in the illustration. Mechanical assembly tip 451 at the distal end of neck 434 permits attaching and releasing of the vertebral component by way of attach/release mechanism 455. The vertebral component 475 can be placed in the back of the spine through a midline incision in the back, for example, via posterior lumbar interbody fusion (PLIF) as shown. The insert instrument 420 can similarly be used in anterior lumbar interbody fusion (ALIF) procedures.

Figure 15:
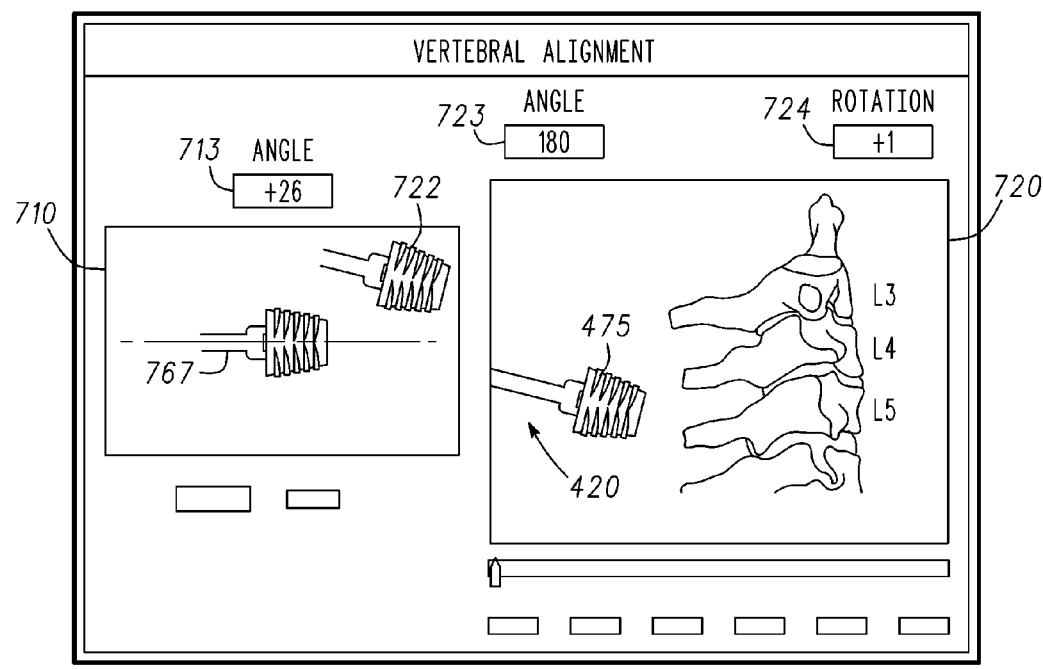
FIG. 15 illustrates a perspective view of a user interface showing the sensorized spinal insert instrument of FIG. 14 in accordance with an example embodiment.

In one method herein contemplated, the position of the cage prior to insertion is optimally defined for example, via 3D imaging or via ultrasonic navigation as described with the wands 510 and 520 with spinal instrument 400 shown in FIGS. 12 and 13. The load sensor 407 (see FIG. 12) is positioned between the vertebra to assess loading forces as described above where an optimal insertion path and trajectory is therein defined. The load forces and path of instrument insertion are recorded. Thereafter as shown in FIG. 14, the insert instrument 420 inserts the final spinal cage 475 according to the recorded path and as based on the load forces. During the insertion the GUI as shown in FIG. 15 navigates the spinal instrument 420 to the recorded insertion point. Spinal insert instrument 420 can be equipped with one or more load sensors serving as a placeholder to a final spinal cage. After placement of spinal cage 475 between the vertebra, release of the spine cage from insert instrument 420, and removal of the insert instrument 420, the open space occupied around the spinal cage is then closed down via rods and pedicle screws on the neighboring vertebra. This compresses the surrounding vertebra onto the spinal cage, and provides stability for verterbral fusion. During this procedure, the GUI 700 of FIG. 15 reports change in spinal anatomy, for example, Lordosis and Kyphosis, due to adjustment of the rods and tightening of the pedicle screws. Notably, the GUI 700 also provides visual feedback indicating which the amount and directions to achieve the planned spinal alignment by way of instrumented adjustments to the rods and screws.

FIG. 15 illustrates user interface 700 showing a perspective view of the sensorized spinal insert instrument 420 of FIG. 14 in a non-limiting example. The user interface 700 is presented by way of the remote system 105 and alignment system 100 (see FIG. 1). The GUI 700 includes a first window 710 and a related second window 720. The second window 720 shows insert instrument 420 and vertebral component 475 in relation to the L4 and L5 vertebrae under evaluation. In this example, a sagital (side) view of the spine column is shown. It indicates a shaft angle 723 and a rotation component 724 which reveal the approach angle and rotation of the insert instrument 420 and vertebral component 475. The second window 720 and corresponding GUI information is presented and updated in real-time during the procedure. It permits the surgeon to visualize the vertebral component 475 of the insert instrument 420 according to the previously sensed load force parameters.

The first window 710 shows a target (desired) sensored head orientation 722 and a current instrument head orientation 767. The target orientation 722 shows the approach angle, rotation and trajectory path previously determined when the spine instrument 400 was used for evaluating loading parameters. The current instrument head orientation 767 shows tracking of the insert instrument 420 currently used to insert the final cage 475. The GUI 700 presents the target orientation model 722 in view of the current instrument head orientation 767 to provide visualization of the previously determined surgical plan.

Recall, FIGS. 10, 11, 12, and 13 illustrated the spine instrument 400 assessed optimal procedural parameters (e.g., angle, rotation, path) in view of determined sensing parameters (e.g., load, force, edge). Once these procedural parameters were determined, the system 100 by way of the GUI 700 now guides the surgeon with the insert instrument 420 to insert the vertebral components 475 (e.g., spine cage, pedicle screw). In one arrangement, the system 100 provides haptic feedback to guide the insert instrument 420 during the insertion procedure. For example, it vibrates when the current approach angle 713 deviates from the target approach angle, provides a visual cue (red/green indication), or when the orientation 767 is not aligned with the target trajectory path 722. Alternatively, vocal feedback can be provided by system 100 to supplement the visual information being provided. The GUI 700 effectively recreates the position and target path on the sensorized insert instrument 420 through visual and haptic feedback based on the previous instrumenting.

The loading, balance, and position can be adjusted during surgery within predetermined quantitatively measured ranges through surgical techniques and adjustments using data from the sensorized devices (e.g., 101, 103, 400, 420, 475) of the alignment and load balance system 100. Both the trial and final inserts (e.g., spine cage, pedicle screw, sensors, etc.) can include the sensing module to provide measured data to the remote system for display. A final insert can also be used to monitor the vertebral joint long term. The data can be used by the patient and health care providers to ensure that the vertebral joint or fused vertebrae is functioning properly during rehabilitation and as the patient returns to an active normal lifestyle. Conversely, the patient or health care provider can be notified when the measured parameters are out of specification. This provides early detection of a spine problem that can be resolved with minimal stress to the patient. The data from final insert can be displayed on a screen in real time using data from the embedded sensing module. In one embodiment, a handheld device is used to receive data from final insert. The handheld device can be held in proximity to the spine allowing a strong signal to be obtained for reception of the data.

A method of distracting a spinal region is disclosed below. The steps of the method can be performed in any order. Reference can be made to FIG. 10, FIG. 11, FIG. 12, FIG. 13, and FIG. 14. An example of placing a prosthetic component such as a spinal cage between vertebrae is used to demonstrate the method but the method is applicable to other muscular-skeletal regions such as the knee, hip, ankle, spine, shoulder, hand, arm, and foot. In general, quantitative measurement data needs to be collected on the spine region. The spinal instrument, alignment devices, and insert instrument disclosed herein can be used to generate a database of quantitative measurement data. At this time there is a dearth of quantitative measurement data due to the lack of active tools and measurement devices. The measurement data generated by the tools during prosthetic component installation can be correlated with other short-term and long-term data to determine the effect of load, position of load, and prosthetic component alignment as it relates to patient health. The system disclosed herein can generate data during prosthetic component installation and is applicable for providing long-term periodic measurement of the implant and spinal region. Thus, the result of the distraction method is to generate sufficient data that supports an installation procedure that reduces recovery time, minimizes failures, improves performance, reliability, and extends device life expectancy.

In a first step, a spinal instrument is inserted to distract the spinal region. The spinal instrument includes sensors for generating quantitative measurement data in real-time during surgery. In a second step, a load applied by the spinal region to the spinal instrument is measured. The spinal instrument has a first height such that the spinal region is distracted to the first height. The system indicates measurement data by visual, audio, or haptic means. In one example, the system discloses that the load measurement from the spinal instrument is outside a predetermined load range. The predetermined load range used by the system to assess the spinal region can be determined by clinical study. For example, the predetermined load range can support device installation by correlating load measurement data to outcomes of the surgical procedure. In general, a measurement outside the predetermined load range may statistically increase a chance of device failure. In a third step, the spinal region is distracted to a second height. In a fourth step, the load applied by the spinal region to the spinal instrument at the second height is measured. The system indicates that the load measurement from the spinal instrument is within the predetermined load range. Having the measured load within the predetermined load range reduces failures due to excessive loading on the prosthetic component. In general, the process can be repeated as many times as required at different distraction heights until the spinal instrument measurement indicates that the measured load is within the predetermined load range.

In a fifth step, at least one of orientation, rotation, angle, or position of the spinal instrument is measured. In one embodiment, the measurement can correspond to the portion of the spinal instrument inserted in the spinal region. For example, the position data can relate to a sensored head of the spinal instrument. The data can be used to place a prosthetic component in a similar position and at the same trajectory as measured by the spinal instrument. In a sixth step, loading applied by the spinal region to the spinal instrument can be monitored on the remote system. In the example, the remote system includes a display that allows viewing of the data in real-time during the procedure. In a seventh step, the height of the spinal instrument can be adjusted. As disclosed, the spinal instrument can include a scissor type mechanism to decrease or increase height of the distraction surfaces. In one embodiment, the handle of the spinal instrument is rotated to change distraction height. The adjustment can be made while monitoring the load data on the remote system in real-time. In general, the height is adjusted until the measured load is within the predetermined load range. In an eighth step, the height is increased or decreased such that the adjusted height corresponds to a height of a prosthetic component. In one embodiment, a prosthetic component having the same distraction height can be placed in the location of the load measurement in the spinal region. The prosthetic component is loaded similarly to the load measurement when aligned to the trajectory and placed in a same location as the spinal instrument.

In a ninth step, the spinal instrument measures a position of applied load. The spinal instrument may have a surface coupled to the spinal region. In the example, more than one sensor is coupled to a surface of the spinal instrument to support position of load measurement. The position of load provides quantitative measurement data on how the force, pressure, or load would be applied to the prosthetic component when placed in the spinal region. For example, an incorrect position of load could produce a situation where the prosthetic component would be unstable in the location and eventually be forced from the spinal region causing a catastrophic failure. In one embodiment, position of load data from the spinal instrument may be used to assess the position for prosthetic component placement. The quantitative data can include a predetermined range or area that corresponds to the measurement surface of the spinal instrument for assessing position of load. In a tenth step, the spinal instrument is moved to a different location in the spinal region when the position of load applied by the spinal region to the spinal instrument is outside a predetermined position range. The new location can be assessed by load magnitude and position of load quantitative data as a site for the prosthetic component.

In an eleventh step, an appropriate location in the spinal region is identified for a prosthetic component when the measured quantitative data falls within the predetermined load range and the predetermined position range. As mentioned previously, placing the prosthetic component in an area of the spinal region measuring within the predetermined load range and the predetermined position range produces positive outcomes and lowers failure rate based on clinical evidence. In a twelfth step, the prosthetic component is placed in the location measured by the spinal instrument. The prosthetic component placed in the location will have an applied load magnitude and position of load by the spinal region similar to that measured by the spinal instrument. The prosthetic component is inserted into the spinal region having a similar trajectory as the spinal instrument. In the example, the trajectory and position of the spinal instrument during the measurement process is recorded. In a thirteenth step, the insertion process of the prosthetic component can be further supported by comparing the trajectory of the prosthetic component to the trajectory of the spinal instrument. In one embodiment, the surgeon can be provided visual, haptic, or audio feedback to aid in the alignment of the prosthetic component to the location. In a fourteenth step, the trajectories of the prosthetic component and the spinal instrument are viewed on a remote system. The remote system can show the actual or simulated position and trajectory of the prosthetic component in relation to the position and trajectory of the spinal instrument when identifying the location in the spinal region. In one embodiment, the surgeon can mimic the trajectory with a device or insert instrument that holds the prosthetic component through a visualization or overlay on the spinal instrument location data displayed on the remote system. As disclosed herein, the spinal instrument can have a mechanism such as a scissor jack that can change the height of the distracting surfaces. A rod for raising and lowering the scissor jack couples to the handle of the spinal instrument. In a fifteenth step, the handle of the spinal instrument can be rotated to change the distraction height. In a sixteenth step, a visual, audio, or haptic signal is provided when the load applied by the spinal region to the spinal instrument are within the predetermined load range. Similarly, in a seventeenth step, a visual, audio, or haptic signal is provided when the load applied by the spinal region to the spinal instrument is within the predetermined position range.

Figure 16:
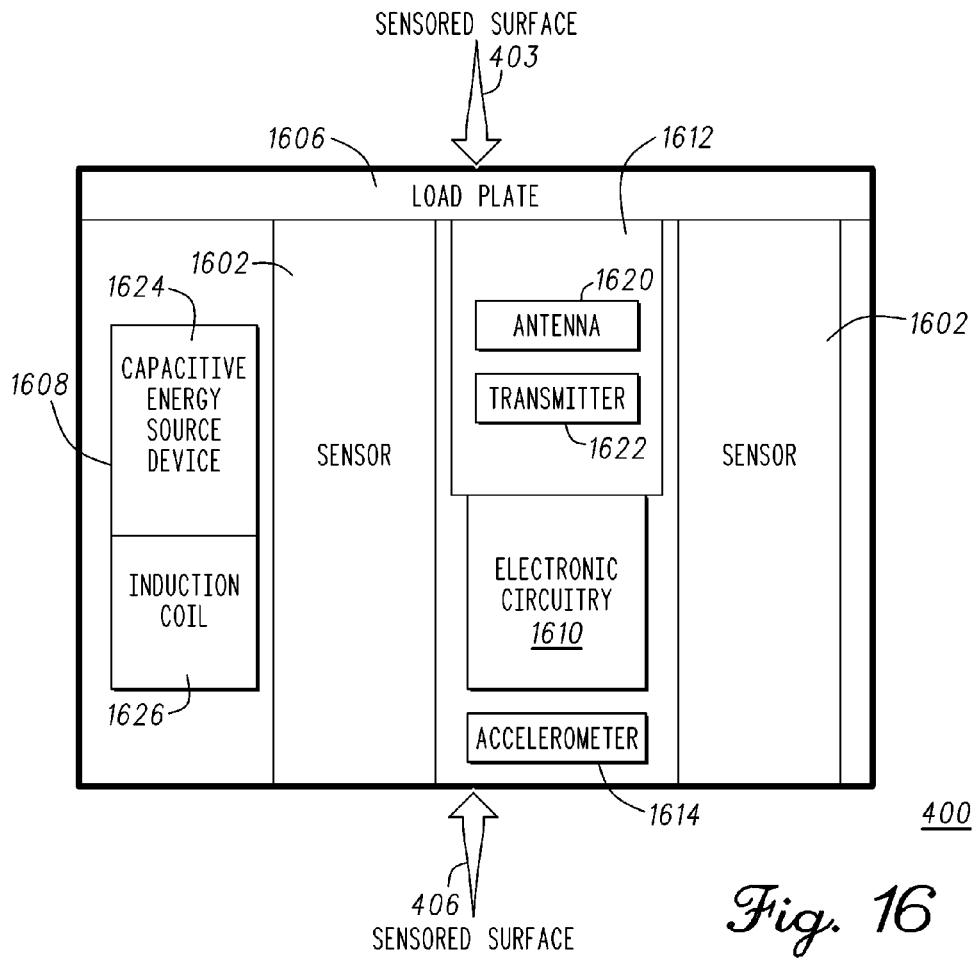
FIG. 16 is a block diagram of the components of the spinal instrument in accordance with an example embodiment.

FIG. 16 is a block diagram of the components of spinal instrument 400 in accordance with an example embodiment. It should be noted that spinal instrument 400 could comprise more or less than the number of components shown. Spinal instrument 400 is a self-contained tool that can measure a parameter of the muscular-skeletal system. In the example, the spinal instrument 400 measures load and position of load when inserted in a spinal region. The active components of spinal instrument 400 include one or more sensors 1602, a load plate 1606, a power source 1608, electronic circuitry 1610, a transceiver 1612, and an accelerometer 1614. In a non-limiting example, an applied compressive force is applied to sensors 1602 by the spinal region and measured by the spinal instrument 400.

The sensors 1602 can be positioned, engaged, attached, or affixed to the surfaces 403 and 406 of spinal instrument 400. In general, a compressive force is applied by the spinal region to surfaces 403 and 406 when inserted therein. The surfaces 403 and 406 couple to sensors 1602 such that a compressive force is applied to each sensor. In one embodiment, the position of applied load to surfaces 403 and 406 can be measured. In the example, three load sensors are used in the sensed head to identify position of applied load. Each load sensor is coupled to a predetermined position on the load plate 1606. The load plate 1606 couples to surface 403 to distribute a compressive force applied to the sensored head of spinal instrument 400 to each sensor. The load plate 1606 can be rigid and does not flex when distributing the force, pressure, or load to sensors 1606. The force or load magnitude measured by each sensor can be correlated back to a location of applied load on the surface 403.

In the example of intervertebral measurement, the sensored head having surfaces 403 and 406 can be positioned between the vertebrae of the spine. Surface 403 of the sensored head couples to a first vertebral surface and similarly the surface 406 couples to a second vertebral surface. Accelerometer 1614 or an external alignment system can be used to measure position and orientation of the sensored head as it is directed into the spinal region. The sensors 1602 couple to the electronic circuitry 1610. The electronic circuitry 1610 comprises logic circuitry, input/output circuitry, clock circuitry, D/A, and A/D circuitry. In one embodiment, the electronic circuitry 1610 comprises an application specific integrated circuit that reduces form factor, lowers power, and increases performance. In general, the electronic circuitry 1610 controls a measurement process, receives the measurement signals, converts the measurement signals to a digital form, supports display on an interface, and initiates data transfer of measurement data. Electronic circuitry 1610 measures physical changes in the sensors 1602 to determine parameters of interest, for example a level, distribution and direction of forces acting on the surfaces 403 and 406. The insert sensing device 400 can be powered by an internal power source 1608. Thus, all the components required to measure parameters of the muscular-skeletal system reside in the spinal instrument 400.

As one example, sensors 1602 can comprise an elastic or compressible propagation structure between a first transducer and a second transducer. The transducers can be an ultrasound (or ultrasonic) resonator, and the elastic or compressible propagation structure can be an ultrasound waveguide. The electronic circuitry 1610 is electrically coupled to the transducers to translate changes in the length (or compression or extension) of the compressible propagation structure to parameters of interest, such as force. The system measures a change in the length of the compressible propagation structure (e.g., waveguide) responsive to an applied force and converts this change into electrical signals, which can be transmitted via the transceiver 1612 to convey a level and a direction of the applied force. For example, the compressible propagation structure has known and repeatable characteristics of the applied force versus the length of the waveguide. Precise measurement of the length of the waveguide using ultrasonic signals can be converted to a force using the known characteristics.

Sensors 1602 are not limited to waveguide measurements of force, pressure, or load sensing. In yet other arrangements, sensors 1602 can include piezo-resistive, compressible polymers, capacitive, optical, mems, strain gauge, chemical, temperature, pH, and mechanical sensors for measuring parameters of the muscular-skeletal system. In an alternate embodiment, a piezo-resistive film sensor can be used for sensing load. The piezo-resistive film has a low profile thereby reducing the form factor required for the implementation. The piezo-resistive film changes resistance with applied pressure. A voltage or current can be applied to the piezo-resistive film to monitor changes in resistance. Electronic circuitry 1610 can be coupled to apply the voltage or current. Similarly, electronic circuitry 1610 can be coupled to measure the voltage and current corresponding to a resistance of the piezo-resistive film. The relation of piezo-resistive film resistance to an applied force, pressure, or load is known. Electronic circuitry 1610 can convert the measured voltage or current to a force, pressure, or load applied to the sensed head. Furthermore, electronic circuitry 1610 can convert the measurement to a digital format for display or transfer for real-time use or for being stored. Electronic circuitry 1610 can include converters, inputs, outputs, and input/outputs that allow serial and parallel data transfer whereby measurements and transmission of data can occur simultaneously. In one embodiment, an ASIC is included in electronic circuitry 1610 that incorporates digital control logic to manage control functions and the measurement process of spinal instrument 400 as directed by the user.

The accelerometer 1614 can measure acceleration and static gravitational pull. Accelerometer 1614 can be single-axis and multi-axis accelerometer structures that detect magnitude and direction of the acceleration as a vector quantity. Accelerometer 1614 can also be used to sense orientation, vibration, impact and shock. The electronic circuitry 1610 in conjunction with the accelerometer 1614 and sensors 1602 can measure parameters of interest (e.g., distributions of load, force, pressure, displacement, movement, rotation, torque, location, and acceleration) relative to orientations of spinal instrument 400. In such an arrangement, spatial distributions of the measured parameters relative to a chosen frame of reference can be computed and presented for real-time display.

The transceiver 1612 comprises a transmitter 1622 and an antenna 1620 to permit wireless operation and telemetry functions. In various embodiments, the antenna 1620 can be configured by design as an integrated loop antenna. The integrated loop antenna is configured at various layers and locations on a printed circuit board having other electrical components mounted thereto. For example, electronic circuitry 1610, power source 1608, transceiver 1612, and accelerometer 1614 can be mounted on a circuit board that is located on or in spinal instrument 400. Once initiated the transceiver 1612 can broadcast the parameters of interest in real-time. The telemetry data can be received and decoded with various receivers, or with a custom receiver. The wireless operation can eliminate distortion of, or limitations on, measurements caused by the potential for physical interference by, or limitations imposed by, wiring and cables coupling the sensing module with a power source or with associated data collection, storage, display equipment, and data processing equipment.

The transceiver 1612 receives power from the power source 1608 and can operate at low power over various radio frequencies by way of efficient power management schemes, for example, incorporated within the electronic circuitry 1610 or the application specific integrated circuit. As one example, the transceiver 1612 can transmit data at selected frequencies in a chosen mode of emission by way of the antenna 1620. The selected frequencies can include, but are not limited to, ISM bands recognized in International Telecommunication Union regions 1, 2 and 3. A chosen mode of emission can be, but is not limited to, Gaussian Frequency Shift Keying, (GFSK), Amplitude Shift Keying (ASK), Phase Shift Keying (PSK), Minimum Shift Keying (MSK), Frequency Modulation (FM), Amplitude Modulation (AM), or other versions of frequency or amplitude modulation (e.g., binary, coherent, quadrature, etc.).

The antenna 1620 can be integrated with components of the sensing module to provide the radio frequency transmission. The antenna 1620 and electronic circuitry 1610 are mounted and coupled to form a circuit using wire traces on a printed circuit board. The antenna 1620 can further include a matching network for efficient transfer of the signal. This level of integration of the antenna and electronics enables reductions in the size and cost of wireless equipment. Potential applications may include, but are not limited to any type of short-range handheld, wearable, or other portable communication equipment where compact antennas are commonly used. This includes disposable modules or devices as well as reusable modules or devices and modules or devices for long-term use.

The power source 1608 provides power to electronic components of the spinal instrument 400. In one embodiment, power source 1608 can be charged by wired energy transfer, short-distance wireless energy transfer or a combination thereof. External power sources for providing wireless energy to power source 1608 can include, but are not limited to, a battery or batteries, an alternating current power supply, a radio frequency receiver, an electromagnetic induction coil, a photoelectric cell or cells, a thermocouple or thermocouples, or an ultrasound transducer or transducers. By way of power source 1608, spinal instrument 400 can be operated with a single charge until the internal energy is drained. It can be recharged periodically to enable continuous operation. The power source 1608 can further utilize power management techniques for efficiently supplying and providing energy to the components of spinal instrument 400 to facilitate measurement and wireless operation. Power management circuitry can be incorporated on the ASIC to manage both the ASIC power consumption as well as other components of the system.

The power source 1608 minimizes additional sources of energy radiation required to power the sensing module during measurement operations. In one embodiment, as illustrated, the energy storage 1608 can include a capacitive energy storage device 1624 and an induction coil 1626. The external source of charging power can be coupled wirelessly to the capacitive energy storage device 1624 through the electromagnetic induction coil or coils 1626 by way of inductive charging. The charging operation can be controlled by a power management system designed into, or with, the electronic circuitry 1610. For example, during operation of electronic circuitry 1610, power can be transferred from capacitive energy storage device 1624 by way of efficient step-up and step-down voltage conversion circuitry. This conserves operating power of circuit blocks at a minimum voltage level to support the required level of performance. Alternatively, power source 1608 can comprise one or more batteries that are housed within spinal instrument 400. The batteries can power a single use of the spinal instrument 400 whereby the device is disposed after it has been used in a surgery.

In one configuration, the external power source can further serve to communicate downlink data to the transceiver 1612 during a recharging operation. For instance, downlink control data can be modulated onto the wireless energy source signal and thereafter demodulated from the induction coil 1626 by way of electronic circuitry 1610. This can serve as a more efficient way for receiving downlink data instead of configuring the transceiver 1612 for both uplink and downlink operation. As one example, downlink data can include updated control parameters that the spinal instrument 400 uses when making a measurement, such as external positional information, or for recalibration purposes. It can also be used to download a serial number or other identification data.

The electronic circuitry 1610 manages and controls various operations of the components of the sensing module, such as sensing, power management, telemetry, and acceleration sensing. It can include analog circuits, digital circuits, integrated circuits, discrete components, or any combination thereof. In one arrangement, it can be partitioned among integrated circuits and discrete components to minimize power consumption without compromising performance. Partitioning functions between digital and analog circuit enhances design flexibility and facilitates minimizing power consumption without sacrificing functionality or performance. Accordingly, the electronic circuitry 1610 can comprise one or more integrated circuits or ASICs, for example, specific to a core signal-processing algorithm.

In another arrangement, the electronic circuitry 1610 can comprise a controller such as a programmable processor, a Digital Signal Processor (DSP), a microcontroller, or a microprocessor, with associated storage memory and logic. The controller can utilize computing technologies with associated storage memory such a Flash, ROM, RAM, SRAM, DRAM or other like technologies for controlling operations of the aforementioned components of the sensing module. In one arrangement, the storage memory may store one or more sets of instructions (e.g., software) embodying any one or more of the methodologies or functions described herein. The instructions may also reside, completely or at least partially, within other memory, and/or a processor during execution thereof by another processor or computer system.

The electronics assemblage also supports testability and calibration features that assure the quality, accuracy, and reliability of the completed wireless sensing module or device. A temporary bi-directional coupling can be used to assure a high level of electrical observability and controllability of the electronics. The test interconnect also provides a high level of electrical observability of the sensing subsystem, including the transducers, waveguides, and mechanical spring or elastic assembly. Carriers or fixtures emulate the final enclosure of the completed wireless sensing module or device during manufacturing processing thus enabling capture of accurate calibration data for the calibrated parameters of the finished wireless sensing module or device. These calibration parameters are stored within the on-board memory integrated into the electronics assemblage.

Applications for the electronic assembly comprising the sensors 1602 and electronic circuitry 1610 may include, but are not limited to, disposable modules or devices as well as reusable modules or devices and modules or devices for long-term use. In addition to non-medical applications, examples of a wide range of potential medical applications may include, but are not limited to, implantable devices, modules within implantable devices, intra-operative implants or modules within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment.

Figure 17:
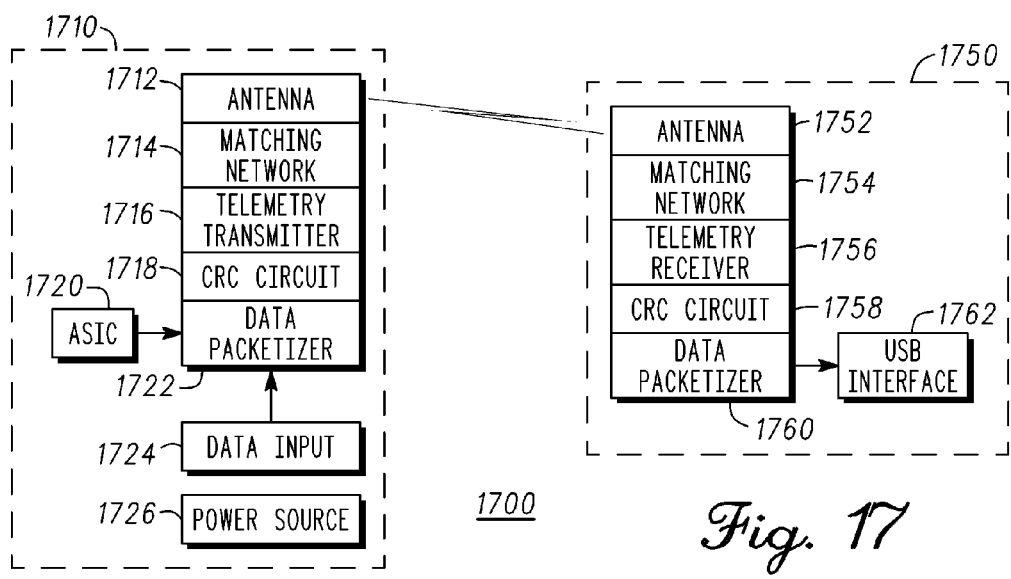
FIG. 17 is a diagram of an exemplary communications system for short-range telemetry in accordance with an example embodiment.

FIG. 17 is a diagram of an exemplary communications system 1700 for short-range telemetry in accordance with an exemplary embodiment. As illustrated, the communications system 1700 comprises medical device communications components 1710 in a spinal instrument and receiving system communications in a processor based remote system. In one embodiment, the receiving remote system communications are in or coupled to a computer or laptop computer that can be viewed by the surgical team during a procedure. The remote system can be external to the sterile field of the operating room but within viewing range to assess measured quantitative data in real time. The medical device communications components 1710 are operatively coupled to include, but not limited to, the antenna 1712, a matching network 1714, a telemetry transceiver 1716, a CRC circuit 1718, a data packetizer 1722, a data input 1724, a power source 1726, and an application specific integrated circuit (ASIC) 1720. The medical device communications components 1710 may include more or less than the number of components shown and are not limited to those shown or the order of the components.

The receiving station communications components 1750 comprise an antenna 1752, a matching network 1754, a telemetry receiver 1756, the CRC circuit 1758, the data packetizer 1760, and optionally a USB interface 1762. Notably, other interface systems can be directly coupled to the data packetizer 1760 for processing and rendering sensor data.

Referring to FIG. 16, the electronic circuitry 1610 is operatively coupled to one or more sensors 602 of the spinal instrument 400. In one embodiment, the data generated by the one or more sensors 602 can comprise a voltage, current, frequency, or count from a mems structure, piezo-resistive sensor, strain gauge, mechanical sensor, pulsed, continuous wave, or other sensor type that can be converted to the parameter being measured of the muscular-skeletal system. Referring back to FIG. 17, the data packetizer 1722 assembles the sensor data into packets; this includes sensor information received or processed by ASIC 1720. The ASIC 1720 can comprise specific modules for efficiently performing core signal processing functions of the medical device communications components 1710. The ASIC 1720 further provides the benefit of reducing a form factor of the tool.

The CRC circuit 1718 applies error code detection on the packet data. The cyclic redundancy check is based on an algorithm that computes a checksum for a data stream or packet of any length. These checksums can be used to detect interference or accidental alteration of data during transmission. Cyclic redundancy checks are especially good at detecting errors caused by electrical noise and therefore enable robust protection against improper processing of corrupted data in environments having high levels of electromagnetic activity. The telemetry transmitter 1716 then transmits the CRC encoded data packet through the matching network 1714 by way of the antenna 1712. The matching networks 1714 and 1754 provide an impedance match for achieving optimal communication power efficiency.

The receiving system communications components 1750 receive transmissions sent by spinal instrument communications components 1710. In one embodiment, telemetry transmitter 1716 is operated in conjunction with a dedicated telemetry receiver 1756 that is constrained to receive a data stream broadcast on the specified frequencies in the specified mode of emission. The telemetry receiver 1756 by way of the receiving station antenna 1752 detects incoming transmissions at the specified frequencies. The antenna 1752 can be a directional antenna that is directed to a directional antenna of components 1710. Using at least one directional antenna can reduce data corruption while increasing data security by further limiting the data is radiation pattern. A matching network 1754 couples to antenna 1752 to provide an impedance match that efficiently transfers the signal from antenna 1752 to telemetry receiver 1756. Telemetry receiver 1756 can reduce a carrier frequency in one or more steps and strip off the information or data sent by components 1710. Telemetry receiver 1756 couples to CRC circuit 1758. CRC circuit 1758 verifies the cyclic redundancy checksum for individual packets of data. CRC circuit 1758 is coupled to data packetizer 1760. Data packetizer 1760 processes the individual packets of data. In general, the data that is verified by the CRC circuit 1758 is decoded (e.g., unpacked) and forwarded to an external data processing device, such as an external computer, for subsequent processing, display, or storage or some combination of these.

The telemetry receiver 1756 is designed and constructed to operate on very low power such as, but not limited to, the power available from the powered USB port 1762, or a battery. In another embodiment, the telemetry receiver 1756 is designed for use with a minimum of controllable functions to limit opportunities for inadvertent corruption or malicious tampering with received data. The telemetry receiver 1756 can be designed and constructed to be compact, inexpensive, and easily manufactured with standard manufacturing processes while assuring consistently high levels of quality and reliability.

In one configuration, the communication system 1700 operates in a transmit-only operation with a broadcasting range on the order of a few meters to provide high security and protection against any form of unauthorized or accidental query. The transmission range can be controlled by the transmitted signal strength, antenna selection, or a combination of both. A high repetition rate of transmission can be used in conjunction with the Cyclic Redundancy Check (CRC) bits embedded in the transmitted packets of data during data capture operations thereby enabling the receiving system to discard corrupted data without materially affecting display of data or integrity of visual representation of data, including but not limited to measurements of load, force, pressure, displacement, flexion, attitude, and position within operating or static physical systems.

By limiting the operating range to distances on the order of a few meters the telemetry transmitter 1716 can be operated at very low power in the appropriate emission mode or modes for the chosen operating frequencies without compromising the repetition rate of the transmission of data. This mode of operation also supports operation with compact antennas, such as an integrated loop antenna. The combination of low power and compact antennas enables the construction of, but is not limited to, highly compact telemetry transmitters that can be used for a wide range of non-medical and medical applications.

The transmitter security as well as integrity of the transmitted data is assured by operating the telemetry system within predetermined conditions. The security of the transmitter cannot be compromised because it is operated in a transmit-only mode and there is no pathway to hack into medical device communications components. The integrity of the data is assured with the use of the CRC algorithm and the repetition rate of the measurements. The risk of unauthorized reception of the data is minimized by the limited broadcast range of the device. Even if unauthorized reception of the data packets should occur there are counter measures in place that further mitigate data access. A first measure is that the transmitted data packets contain only binary bits from a counter along with the CRC bits. A second measure is that no data is available or required to interpret the significance of the binary value broadcast at any time. A third measure that can be implemented is that no patient or device identification data is broadcast at any time.

The telemetry transmitter 1716 can also operate in accordance with some FCC regulations. According to section 18.301 of the FCC regulations the ISM bands within the USA include 6.78, 13.56, 27.12, 30.68, 915, 2450, and 5800 MHz as well as 24.125, 61.25, 122.50, and 245 GHz. Globally other ISM bands, including 433 MHz, are defined by the International Telecommunications Union in some geographic locations. The list of prohibited frequency bands defined in 18.303 are "the following safety, search and rescue frequency bands is prohibited: 490-510 kHz, 2170-2194 kHz, 8354-8374 kHz, 121.4-121.6 MHz, 156.7-156.9 MHz, and 242.8-243.2 MHz." Section 18.305 stipulates the field strength and emission levels ISM equipment must not exceed when operated outside defined ISM bands. In summary, it may be concluded that ISM equipment may be operated worldwide within ISM bands as well as within most other frequency bands above 9 KHz given that the limits on field strengths and emission levels specified in section 18.305 are maintained by design or by active control. As an alternative, commercially available ISM transceivers, including commercially available integrated circuit ISM transceivers, may be designed to fulfill these field strengths and emission level requirements when used properly.

In one configuration, the telemetry transmitter 1716 can also operate in unlicensed ISM bands or in unlicensed operation of low power equipment, wherein the ISM equipment (e.g., telemetry transmitter 1716) may be operated on ANY frequency above 9 kHz except as indicated in Section 18.303 of the FCC code.

Wireless operation eliminates distortion of, or limitations on, measurements caused by the potential for physical interference by, or limitations imposed by, wiring and cables coupling the wireless sensing module or device with a power source or with data collection, storage, or display equipment. Power for the sensing components and electronic circuits is maintained within the wireless sensing module or device on an internal energy storage device. This energy storage device is charged with external power sources including, but not limited to, a battery or batteries, super capacitors, capacitors, an alternating current power supply, a radio frequency receiver, an electromagnetic induction coil, a photoelectric cell or cells, a thermocouple or thermocouples, or an ultrasound transducer or transducers. The wireless sensing module may be operated with a single charge until the internal energy source is drained or the energy source may be recharged periodically to enable continuous operation. The embedded power supply minimizes additional sources of energy radiation required to power the wireless sensing module or device during measurement operations. Telemetry functions are also integrated within the wireless sensing module or device. Once initiated the telemetry transmitter continuously broadcasts measurement data in real time. Telemetry data may be received and decoded with commercial receivers or with a simple, low cost custom receiver.

Figure 18:
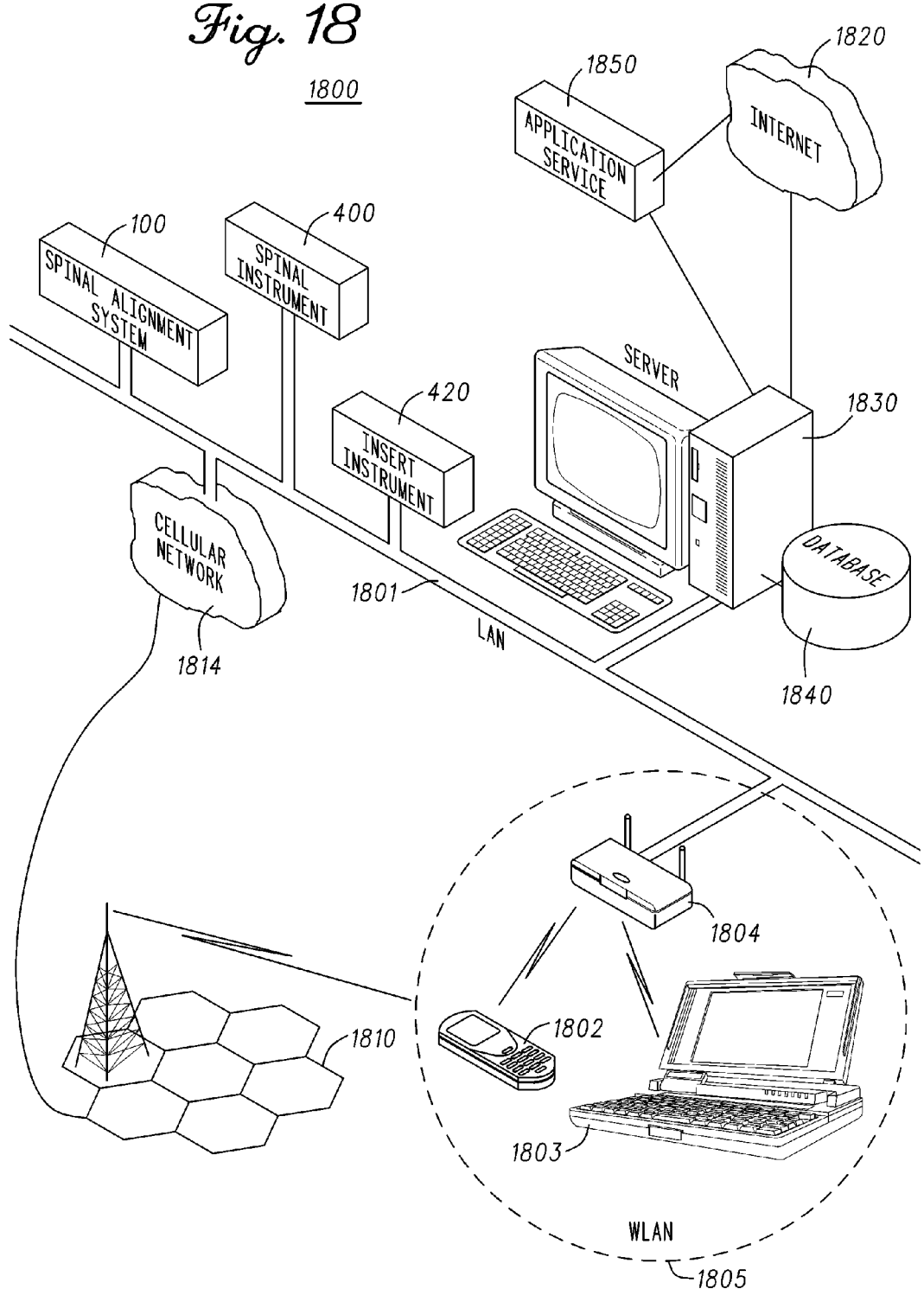
FIG. 18 illustrates a communication network for measurement and reporting in accordance with an example embodiment.

FIG. 18 illustrates a communication network 1800 for measurement and reporting in accordance with an example embodiment. Briefly, the communication network 1800 expands spinal alignment system 100, spinal instrument 400, and insert instrument 420 to provide broad data connectivity to other devices or services. As illustrated, spinal alignment system 100, spinal instrument 400, and insert instrument 420 can be communicatively coupled to the communications network 1800 and any associated systems or services.

As one example, spinal alignment system 100, spinal instrument 400, and insert instrument 420 can share its parameters of interest (e.g., distributions of load, force, pressure, displacement, movement, rotation, torque and acceleration) with remote services or providers, for instance, to analyze or report on surgical status or outcome. In the case that a sensor system is permanently implanted, the data from the sensor can be shared for example with a service provider to monitor progress or with plan administrators for surgical planning purposes or efficacy studies. The communication network 1800 can further be tied to an Electronic Medical Records (EMR) system to implement health information technology practices. In other embodiments, the communication network 1800 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 1800 can provide wired or wireless connectivity over a Local Area Network (LAN) 1801, a Wireless Local Area Network (WLAN) 1805, a Cellular Network 1814, and/or other radio frequency (RF) system. The LAN 1801 and WLAN 1805 can be communicatively coupled to the Internet 1820, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 1800 can utilize common computing and communications technologies to support circuit-switched and/or packet-switched communications. Each of the standards for Internet 1820 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 1814 can support voice and data services over a number of access technologies such as GSM-GPRS, EDGE, CDMA, UMTS, WiMAX, 2G, 3G, WAP, software defined radio (SDR), and other known technologies. The cellular network 1814 can be coupled to base receiver 1810 under a frequency-reuse plan for communicating with mobile devices 1802.

The base receiver 1810, in turn, can connect the mobile device 1802 to the Internet 1820 over a packet switched link. The internet 1820 can support application services and service layers for distributing data from spinal alignment system 100, spinal instrument 400, and insert instrument 420 to the mobile device 502. The mobile device 1802 can also connect to other communication devices through the Internet 1820 using a wireless communication channel.

The mobile device 1802 can also connect to the Internet 1820 over the WLAN 1805. Wireless Local Access Networks (WLANs) provide wireless access within a local geographical area. WLANs are typically composed of a cluster of Access Points (APs) 1804 also known as base stations. Spinal alignment system 100, spinal instrument 400, and insert instrument 420 can communicate with other WLAN stations such as laptop 1803 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etc.).

By way of the communication network 1800, spinal alignment system 100, spinal instrument 400, and insert instrument 420 can establish connections with a remote server 1830 on the network and with other mobile devices for exchanging data. The remote server 1830 can have access to a database 1840 that is stored locally or remotely and which can contain application specific data. The remote server 1830 can also host application services directly, or over the internet 1820.

Figure 19:
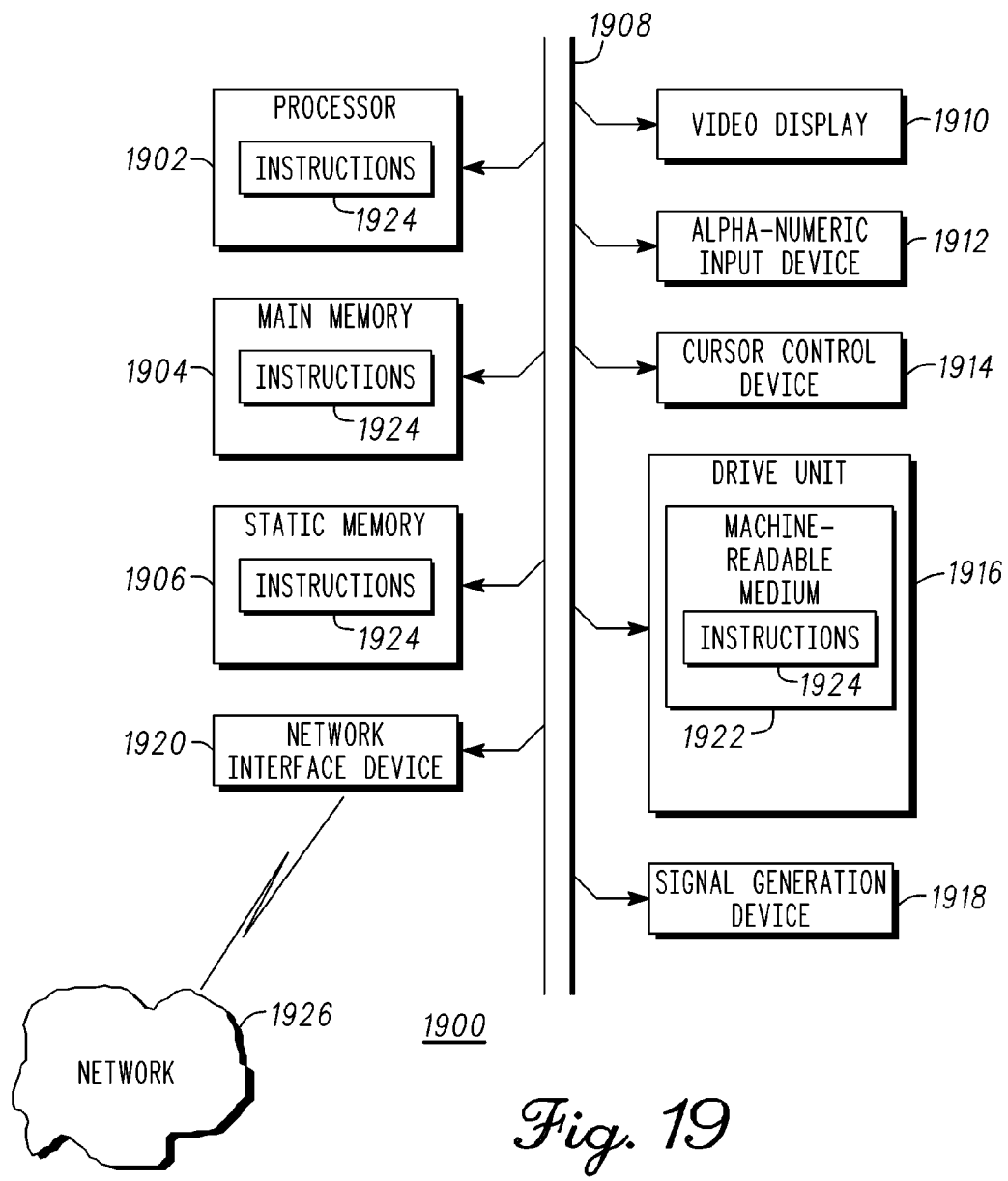
FIG. 19 depicts an exemplary diagrammatic representation of a machine in the form of a computer system within which a set of instructions, when executed, may cause the machine to perform any one or more of the methodologies disclosed herein.

FIG. 19 depicts an exemplary diagrammatic representation of a machine in the form of a computer system 1900 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system 1900 may include a processor 1902 (e.g., a central processing unit (CPU), a graphics processing unit (GPU, or both), a main memory 1904 and a static memory 1906, which communicate with each other via a bus 1908. The computer system 1900 may further include a video display unit 1910 (e.g., a liquid crystal display (LCD), a flat panel, a solid-state display, or a cathode ray tube (CRT)). The computer system 1900 may include an input device 1912 (e.g., a keyboard), a cursor control device 1914 (e.g., a mouse), a disk drive unit 1916, a signal generation device 1918 (e.g., a speaker or remote control) and a network interface device 1920.

The disk drive unit 1916 may include a machine-readable medium 1922 on which is stored one or more sets of instructions (e.g., software 1924) embodying any one or more of the methodologies or functions described herein, including those methods illustrated above. The instructions 1924 may also reside, completely or at least partially, within the main memory 1904, the static memory 1906, and/or within the processor 1902 during execution thereof by the computer system 1900. The main memory 1904 and the processor 1902 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a processor, digital signal processor, or logic circuitry. Furthermore, software implementations can include, but not limited to, distributed processing or component/object distributed processing, parallel processing, or virtual machine processing can also be constructed to implement the methods described herein.

The present disclosure contemplates a machine readable medium containing instructions 1924, or that which receives and executes instructions 1924 from a propagated signal so that a device connected to a network environment 1926 can send or receive voice, video or data, and to communicate over the network 1926 using the instructions 1924. The instructions 1924 may further be transmitted or received over a network 1926 via the network interface device 1920.

While the machine-readable medium 1922 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A spinal measurement system comprising:
   a spinal distractor configured to distract a region of a spine, the spine distractor comprising:
   a handle coupled to a shaft and the shaft coupled to a sensored head wherein the sensored head includes at least one load sensor to measure loading applied by the spine in the region distracted by the spinal distractor;
   an electronic assembly configured to couple to the sensored head wherein the electronic assembly includes a transmitter configured to transmit load measurement data;

an insert instrument configured to place a spine cage comprising:
a shaft;
a tip coupled to a distal end of the; and
a handle coupled to the shaft wherein the insert instrument is configured to place a spinal cage in the region distracted by the spinal distractor;
a position measurement system configured to monitor a position of the spinal distractor, the insert instrument, or the spine, over a range of five meters or less wherein the position measurement system is configured to transmit position measurements in real-time;
a remote system wherein the remote system comprises a computer wherein the computer includes software and memory, wherein the computer is configured to receive load measurement data, and wherein the computer is configured to receive position data of the spinal distractor, the insert instrument, or the spine; and
wherein the electronic assembly is configured to couple to the insert instrument, wherein the electronic assembly is configured to transmit position measurements in real-time, and wherein the computer is configured to compare the path, positions, and trajectory of the insert instrument to the path, positions, and trajectory of the spinal distractor.

2. The system of claim 1 wherein the sensored head of the spinal distractor has a convex surface.

3. The system of claim 1 wherein the position measurement system is in the electronic assembly.

4. The system of claim 3 wherein the electronic assembly is in the handle of the spinal distractor.

5. The system of claim 3 wherein the position measurement system comprises a plurality of accelerometers.

6. The system of claim 3 wherein the electronic assembly is removable from the spinal distractor wherein the computer is configured to receive position measurements of the spinal distractor, wherein the computer stores the position measurements in the memory coupled to the computer, wherein the computer is configured to identify a path, positions, and trajectory of the spinal distractor to the region distracted by the spinal distractor.

7. The system of claim 1 wherein the sensored head of the spinal distractor includes a plurality of load sensors and wherein the spinal distractor is configured to measure load magnitude and position of load in the region distracted by the spinal distractor.

8. The system of claim 1 wherein the position measurement system comprises a receiver and at least one wand, wherein the receiver is in a field of view of a surgical area, wherein the receiver is acoustically coupled to the at least one wand to track the at least one wand orientation and location, and wherein the at least one wand comprises at least three ultrasonic tranducers.

9. The system of claim 8 wherein the tip of the at least one wand can include a sensor.

10. The system of claim 8 wherein the position measurement system measures a time of flight and a differential time of flight of acoustic signals from the at least one wand to measure distance and position of the at least one wand.

11. The spinal measurement system according to claim 8 wherein the at least one wand can be coupled to the spine.

12. The system of claim 8 wherein the at least one wand can be coupled to the spinal distractor.

13. The system of claim 8 wherein the at least one wand can be coupled to the insert instrument.

14. The system of claim 8 wherein a tip of the at least one wand is configured to touch an object to register a point within the surgical area.

* * * * *